(12) United States Patent
Ueda et al.

(10) Patent No.: US 7,595,428 B2
(45) Date of Patent: Sep. 29, 2009

(54) WATER-ABSORBING AGENT COMPOSITION AND METHOD FOR PRODUCTION THEREOF, ABSORPTIVE ARTICLE AND ABSORBING MATERIAL

(75) Inventors: Hiroko Ueda, Himeji (JP); Katsuyuki Wada, Himeji (JP); Yoshio Irie, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 756 days.

(21) Appl. No.: 10/148,436

(22) PCT Filed: Nov. 21, 2001

(86) PCT No.: PCT/JP01/10172

§ 371 (c)(1),
(2), (4) Date: May 30, 2002

(87) PCT Pub. No.: WO02/42379

PCT Pub. Date: May 30, 2002

(65) Prior Publication Data

US 2003/0004479 A1    Jan. 2, 2003

(30) Foreign Application Priority Data

Nov. 22, 2000 (JP) .............................. 2000-356481
Dec. 28, 2000 (JP) .............................. 2000-400544

(51) Int. Cl.
*A61F 13/15* (2006.01)
(52) U.S. Cl. ...................................... 604/359; 604/360
(58) Field of Classification Search ................. 604/359, 604/360
See application file for complete search history.

(56) References Cited

U.S. PATENT DOCUMENTS 1,932,383 A * 10/1933 Richardson ................. 604/375
5,229,488 A    7/1993 Nagasuna et al. ........... 528/487

(Continued)

FOREIGN PATENT DOCUMENTS

EP          0618005       10/1994

(Continued)

*Primary Examiner*—Tatyana Zalukaeva
*Assistant Examiner*—Lynne Anderson
(74) *Attorney, Agent, or Firm*—Roylance, Abrams, Berdo & Goodman, L.L.P.

(57) ABSTRACT

The present invention has an object to provide a particulate water-absorbing composition, a production process therefor, and an absorbent article comprising this particulate water-absorbing composition, wherein the particulate water-absorbing composition causes little coloring of other materials and further is of high safety, and can provide excellent deodorizability and excellent absorption properties to absorbent articles such as diapers in the case where combined into the absorbent articles. As a means of achieving this object, a particulate water-absorbing composition according to the present invention is characterized by comprising a plant powder and a water-absorbent resin, wherein a surface portion and/or its vicinity of the water-absorbent resin is surface-treated with a crosslinking agent, and wherein the particulate water-absorbing composition exhibits an offensive-odor removal index of not less than 180 wherein the offensive-odor removal index is represented by the following equation: offensive-odor removal index=1.1×hydrogen sulfide removal ratio+2.0×methylmercaptan removal ratio+0.3×ammonia removal ratio.

46 Claims, 1 Drawing Sheet

U.S. PATENT DOCUMENTS

| | | | | |
|---|---|---|---|---|
| 5,422,405 | A | * | 6/1995 | Dairoku et al. ............. 525/384 |
| 5,526,771 | A | * | 6/1996 | Ito ............................ 119/172 |
| 5,980,879 | A | | 11/1999 | Hiroki et al. ............... 424/76.1 |
| 6,056,949 | A | * | 5/2000 | Menzi et al. ............... 424/76.1 |
| 6,183,850 | B1 | * | 2/2001 | Lauer ...................... 428/304.4 |
| 6,261,679 | B1 | * | 7/2001 | Chen et al. ............... 428/317.9 |
| 6,765,124 | B2 | * | 7/2004 | Wada et al. ................. 604/359 |
| 2004/0048955 | A1 | * | 3/2004 | Wada et al. .................... 524/9 |

FOREIGN PATENT DOCUMENTS

| | | |
|---|---|---|
| EP | 1053732 | 11/2000 |
| EP | 1080735 | 3/2001 |
| EP | 1099474 | 5/2001 |
| EP | 1 108 745 | 6/2001 |
| JP | 5938271 | 3/1984 |
| JP | 59105448 | 6/1984 |
| JP | 59-115741 | 7/1984 |
| JP | 60158861 | 8/1985 |
| JP | 60174155 | 9/1985 |
| JP | 63135501 | 6/1988 |
| JP | 241155 | 2/1990 |
| JP | 359075 | 3/1991 |
| JP | 4139104 | 5/1992 |
| JP | 5179053 | 7/1993 |
| JP | 5-293136 | 11/1993 |
| JP | 6287220 | 10/1994 |
| JP | 7165981 | 6/1995 |
| JP | 8176338 | 7/1996 |
| JP | 9-241998 | 9/1997 |
| JP | 10314286 | 12/1998 |
| JP | 2881739 | 2/1999 |
| JP | 11116829 | 4/1999 |
| JP | 11241030 | 9/1999 |
| JP | 11-286611 | 10/1999 |
| JP | 200015093 | 1/2000 |
| JP | 200051339 | 2/2000 |
| JP | 200079159 | 3/2000 |
| JP | 2001-039888 | 2/2001 |
| JP | 200129384 | 2/2001 |
| JP | 2001-064526 | 3/2001 |
| JP | 2001-079073 | 3/2001 |
| JP | 200170785 | 3/2001 |

* cited by examiner

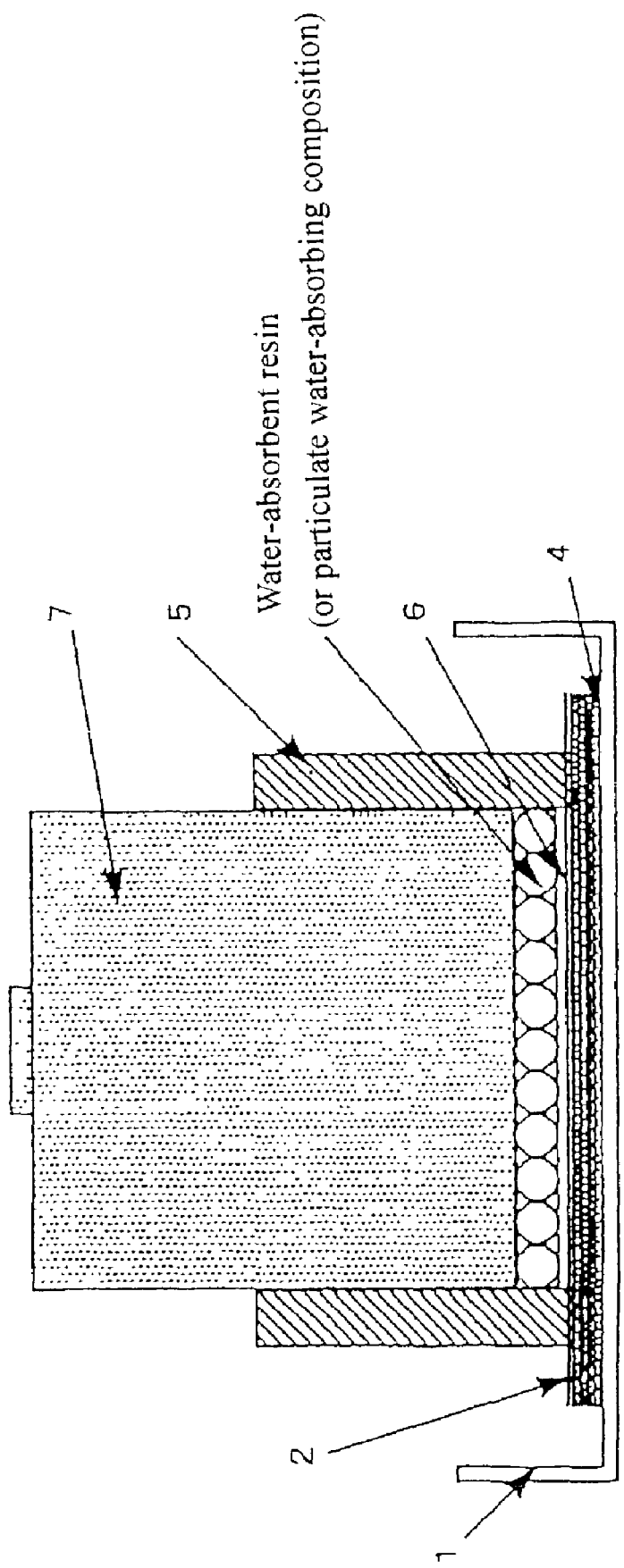

WATER-ABSORBING AGENT COMPOSITION AND METHOD FOR PRODUCTION THEREOF, ABSORPTIVE ARTICLE AND ABSORBING MATERIAL

TECHNICAL FIELD

The present invention relates to a particulate water-absorbing composition, an absorbent article, and an absorbent structure, wherein the absorbent article and the absorbent structure comprise the particulate water-absorbing composition. More specifically, the invention relates to a particulate water-absorbing composition, an absorbent article, and an absorbent structure wherein the particulate water-absorbing composition can provide especially excellent deodorizability and excellent absorption properties, and further, gel stability, to absorbent structures for sanitary materials such as disposable diapers, sanitary napkins and incontinent pads in the case where used in the absorbent structures.

BACKGROUND ART

In recent years, water-absorbent resins are widely used as among components of sanitary materials, such as disposable diapers, sanitary napkins and incontinent pads, for the purpose of causing the water absorbent resins to absorb body liquids.

As to the above water-absorbent resins, the following are known as their examples: partially-neutralized and crosslinked poly(acrylic acids); hydrolyzed graft polymers of starch-acrylonitrile; neutralized graft polymers of starch-acrylic acid; saponified copolymers of vinyl acetate-acrylate esters; crosslinked polymers of carboxymethyl cellulose; hydrolyzed copolymers of acrylonitrile or acrylamide, or crosslinked polymers of these hydrolyzed copolymers; crosslinked polymers of cationic monomers; crosslinked copolymers of isobutylene-maleic acid; and crosslinked copolymers of 2-acrylamido-2-methylpropanesulfonic acid-acrylic acid.

It is said that the above water-absorbent resins are desired to have water absorption properties such as, upon contact with aqueous liquids (e.g. body fluids), high absorption capacity, excellent absorption rate, liquid permeability, gel strength of swollen gel, and suction quantity to suck up water from a base material containing aqueous liquids.

In addition to the above, various attempts are made to provide added functions to the water-absorbent resins by adding thereto deodorizable and antibacterial compounds.

The deodorization is one of performances desirable to absorbent articles, and studies are made to enhance the deodorizability of the water-absorbent resins. Proposed as methods for providing the deodorizability are, for example, methods in which the water-absorbent resins are allowed to contain the follow materials: active carbon (JP-A-105448/1984); extracts from leaves of Theaceae plants (JP-A-158861/1985); essences extracted from coniferous trees (JP-A-241030/1999); manufactured tea (JP-A-041155/1990); tannic acid and complex silicate salt compounds (JP-A-116829/1999).

However, as to the method in which the water-absorbent resins are allowed to contain the active carbon (JP-A-105448/1984), there are problems in that the deodorizing effect is displayed by adsorption of malodorous components to the active carbon, but that the absorbency of the active carbon deteriorates with the passage of time so much that the active carbon becomes deactivated in a period of from the provision to absorbent articles till absorption of urine by the absorbent articles during their practical use. In addition, there are also significant problems in that the active carbon causes black coloring of diapers in the case where used for the diapers.

As to the method in which the water-absorbent resins are allowed to contain the extracts from leaves of Theaceae plants (JP-A-158861/1985), the problems of coloring are improved, but the effect during the practical use is low. In addition, production costs increase because of the extraction from leaves of plants.

As to the method in which the water-absorbent resins are allowed to contain the essences extracted from coniferous trees (JP-A-241030/1999), essential oils such as essences extracted from trees have strong smells peculiar to them and therefore, during the practical use, for example, display a high deodorizing effect of rendering the odor of urine indistinguishable. In such a case, the deodorizing effect is mainly from an odor-masking effect. The deodorization by masking involves the smells peculiar to the essential oils. And there are differences between individuals' tastes for smells, so the essential oils are not suitable as consumer materials aimed at many people. In addition, the essential oils involve production costs.

As to the method in which the water-absorbent resins are allowed to contain the tannic acid and the complex silicate salt compounds (JP-A-116829/1999), the removal effect is displayed upon specific malodorous substances, but the deodorizing effect during the practical use of absorbent articles cannot be said to be enough, probably because there is no effect upon bad smells included in actual body fluids such as urine.

As to the method in which the water-absorbent resins are allowed to contain the manufactured tea (JP-A-041155/1990), the deodorizing effect of the manufactured tea itself is good, but still the deodorizing effect during the practical use of absorbent articles could not be said to be enough, probably because of performances of water-absorbent resins being used.

In addition, by reason of the use for such as absorbent articles, the provision with the deodorizability is always desired to involve high safety.

DISCLOSURE OF THE INVENTION

Object of the Invention

An object of the present invention is to provide a particulate water-absorbing composition, a production process therefor, an absorbent article, and an absorbent structure, wherein the particulate water-absorbing composition causes little coloring of other materials and further is of high safety, and can provide excellent deodorizability and excellent absorption properties to absorbent articles such as diapers in the case where combined into the absorbent articles.

SUMMARY OF THE INVENTION

The present inventors diligently studied water-absorbing agents from the point of view of excellent deodorizability and excellent absorption properties in the case where the water-absorbing agents are combined into absorbent articles such as diapers. As a result, the inventors have completed the present invention by finding out that if a plant powder and a water-absorbent resin which has specific properties are combined together to provide specific performance, then the above object can be achieved.

That is to say, a particulate water-absorbing composition, according to the present invention, is characterized by comprising a plant powder and a water-absorbent resin, wherein a surface portion and/or its vicinity of the water-absorbent resin is surface-treated with a crosslinking agent, and wherein the particulate water-absorbing composition exhibits an offensive-odor removal index of not less than 180 wherein the offensive-odor removal index is represented by the following equation:

offensive-odor removal index=1.1×hydrogen sulfide removal ratio+2.0×methylmercaptan removal ratio+0.3×ammonia removal ratio.

In the above particulate water-absorbing composition according to the present invention, the plant powder favorably comprises a powder of a Tracheophyta plant, or a spice, or a tea leaf and/or a residue of extraction therefrom.

In the above particulate water-absorbing composition according to the present invention, the content of the plant powder is favorably in the range of 0.001 to 20 weight parts per 100 weight parts of the solid content of the water-absorbent resin.

The above particulate water-absorbing composition, according to the present invention, favorably exhibits an absorption capacity of 25 to 60 g/g, a suction index of not less than 14 g/g under a load, and an absorption rate of not more than 60 seconds.

In addition, another particulate water-absorbing composition, according to the present invention, is characterized by: comprising a plant powder and a water-absorbent resin; and exhibiting an absorption capacity of 25 to 60 g/g, a suction index of not less than 14 g/g under a load, and an absorption rate of not more than 60 seconds; and exhibiting an offensive-odor removal index of not less than 180 wherein the offensive-odor removal index is represented by the following equation:

offensive-odor removal index=1.1×hydrogen sulfide removal ratio+2.0×methylmercaptan removal ratio+0.3×ammonia removal ratio.

The particulate water-absorbing composition, according to the present invention, is favorably used for sanitary materials.

A process for producing a particulate water-absorbing composition, according to the present invention, is characterized by comprising the step of adding a plant powder to a water-absorbent resin that exhibits an absorption capacity of 25 to 60 g/g, a suction power of not less than 9 g/g under a load, and an absorption rate of not more than 60 seconds.

An absorbent article, according to the present invention, comprises an absorbent layer, a liquid-permeable surface sheet, and a liquid-impermeable back sheet, wherein the absorbent layer includes the present invention particulate water-absorbing composition.

An absorbent structure, according to the present invention, comprises a hydrophilic fiber, a plant powder, and a water-absorbent resin; and is characterized by exhibiting an offensive-odor removal index of not less than 180 as a particulate water-absorbing composition including a mixture of the plant powder and the water-absorbent resin, wherein the offensive-odor removal index is represented by the following equation:

offensive-odor removal index=1.1×hydrogen sulfide removal ratio+2.0×methylmercaptan removal ratio+0.3×ammonia removal ratio.

The absorbent structure, according to the present invention, favorably comprises the particulate water-absorbing composition in which the plant powder is held by the water-absorbent resin.

DETAILED DESCRIPTION OF THE INVENTION

Hereinafter, the present invention is explained in detail.

Used as the water-absorbent resin in the present invention is favorably a water-absorbent resin of which a surface portion and/or its vicinity is surface-treated with a crosslinking agent, specifically, treated by crosslinking with a crosslinking agent reactable with a functional group of the water-absorbent resin, and/or which exhibits an absorption capacity of 25 to 60 g/g, a suction power of not less than 9 g/g under a load, and an absorption rate of not more than 60 seconds.

As to the absorption properties of the water-absorbent resin, it is favorable, for enhancing the effect of providing the deodorizability to the whole diaper, to combine together a plant powder and a water-absorbent resin which satisfies all the properties such as the absorption capacity of 25 to 60 g/g, the suction power of not less than 9 g/g under a load, and the absorption rate of not more than 60 seconds. Although not clear, the cause is considered to be probably that if the water-absorbent resin is limited to such as exhibits the specific absorption capacity, suction power under a load, and absorption rate and if such a water-absorbent resin is combined with the plant powder, then the optimum balance between the action of the plant powder and the liquid absorption upon contact with urine is achieved.

The water-absorbent resin of which a surface portion and/or its vicinity is surface-crosslinked with a crosslinking agent, used in the present invention, is generally obtained by a production process comprising the step of subjecting a water-absorbent resin to a surface-crosslinking treatment.

The water-absorbent resin in the present invention means a water-swellable and water-insoluble crosslinked polymer which absorbs water to form an anionic, nonionic, cationic, or their hybrid water-insoluble hydrogel. In addition, the particulate water-absorbing composition, as referred to in the present invention, means a material which contains the water-absorbent resin in a major proportion, favorably, of not less than 70 weight %, more favorably, of not less than 80 weight %, and absorbs water.

Incidentally, the term "water-swellable" means that the material is able to absorb at least 2 times, favorably 10 to 3,000 times, more favorably 50 to 2,000 times, as large a quantity of water as its own weight (solid content) in ion-exchanged water, and the term "water-insoluble" means that the uncrosslinked water-extractable content in the water-absorbent resin is not more than 50 weight %, favorably not more than 25 weight %, more favorably not more than 20 weight %, still more favorably not more than 15 weight %, particularly favorably not more than 10 weight %.

A method for measuring the water-extractable content is specified in EDANA RECOMMENDED TEST METHODS 470, 1-99 EXTRACTABLES of EUROPEAN DISPOSABLES AND NONWOVENS ASSOCIATION.

Examples of such water-absorbent resins include one or mixtures of the following materials: partially-neutralized and crosslinked poly(acrylic acids); hydrolyzed graft polymers of starch-acrylonitrile; neutralized graft polymers of starch-acrylic acid; saponified copolymers of vinyl acetate-acrylate esters; hydrolyzed copolymers of acrylonitrile or acrylamide, or crosslinked polymers of these hydrolyzed copolymers; modified polymers of carboxyl-group-containing crosslinked poly(vinyl alcohols); and crosslinked copolymers of isobutylene-maleic anhydride.

These water-absorbent resins may be used either alone respectively or in combinations with each other, but, in particular, one or mixtures of those which have a carboxyl group are favorable, and it is typically favorable that the water-absorbent resin comprises a polymer (water-swellable crosslinked polymer of poly(acrylic acid (salt))) as the main component which polymer is obtained by a process including the steps of polymerizing monomers including acrylic acid and/or its salt (neutralized product) as the main component and then crosslinking the resultant polymer. In addition, these water-absorbent resins may be either water-containing hydrogels, or powders obtained by a process including the steps of: drying the hydrogels, if necessary; and usually pulverizing them before and/or after the drying step.

The above-mentioned water-absorbent resin, for example, can be obtained by a process including the steps of: polymerizing or copolymerizing at lease one monomer selected from the group consisting of unsaturated carboxylic acids, such as (meth)acrylic acid, maleic acid, maleic anhydride, fumaric acid, crotonic acid, itaconic acid, and β-acryloyloxypropionic acid, and neutralized products thereof; and then, if need be, subjecting the resultant polymer to operations, such as pulverization and classification, to arrange its particle diameters.

The neutralization ratio of the above acid group is favorably adjusted into the range of 30 to 100 mol %, more favorably 60 to 90 mol %, still more favorably 65 to 75 mol %. The neutralization of the acid group may be carried out either by neutralization of an acid-group-containing monomer in an aqueous solution before polymerization, or by neutralization of an aqueous solution of the polymer, in other words, by post-neutralization of a polymer gel, or both neutralizations may be used jointly with each other. Favorable examples of salts being neutralized include those of sodium, lithium, potassium, ammonia, and amines.

As to the monomer, (meth)acrylic acid and their neutralized products are preferable of the above monomers. The weight-average particle diameter is favorably in the range of 100 to 600 μm, more favorably 200 to 500 μm, and the proportion of particles having particle diameters of smaller than 106 μm is not more than 10 weight %, favorably not more than 5 weight %, more favorably not more than 3 weight %.

Furthermore, the above-mentioned water-absorbent resin may be a copolymer of the above-mentioned monomer and another monomer copolymerizable therewith. Specific examples of the above other monomer include: anionic unsaturated monomers, such as vinylsulfonic acid, styrenesulfonic acid, 2-(meth)acrylamido-2-methylpropanesulfonic acid, 2-(meth)acryloylethanesulfonic acid, and 2-(meth)acryloylpropanesulfonic acid, and salts thereof, nonionic hydrophilic-group-containing unsaturated monomers such as acrylamide, methacrylamide, N-ethyl(meth)acrylamide, N-n-propyl (meth)acrylamide, N-isopropyl(meth)acrylamide, N,N-dimethyl(meth)acrylamide, 2-hydroxyethyl (meth)acrylate, 2-hydroxypropyl(meth)acrylate, methoxypolyethylene glycol (meth)acrylate, polyethylene glycol mono(meth)acrylate, vinylpyridine, N-vinylpyrrolidone, N-acryloylpiperidine, and N-acryloylpyrrolidine; and cationic unsaturated monomers such as N,N-dimethylaminoethyl(meth)acrylate, N,N-diethylaminoethyl(meth)acrylate, N,N-dimethylaminopropyl(meth)acrylate, N,N-dimethylaminopropyl(meth)acrylamide, and quaternary salts thereof.

It is favorable that the water-absorbent resin is such as internally crosslinked by a reaction or copolymerization with a crosslinking agent having at least two polymerizable unsaturated groups or at least two reactive groups. In addition, the water-absorbent resin may be a self-crosslinking type which does not need any crosslinking agent.

Specific examples of the above crosslinking agent (which might be referred to as internal-crosslinking agent) include N,N'-methylenebis(meth)acrylamide, (poly)ethylene glycol di(meth)acrylate, (poly)propylene glycol di(meth)acrylate, trimethylolpropane di(meth)acrylate, trimethylolpropane tri (meth)acrylate, glycerol tri(meth)acrylate, glycerol acrylate methacrylate, ethylene-oxide-modified trimethylolpropane tri(meth)acrylate, pentaerythritol tetra(meth)acrylate, dipentaerythritol hexa(meth)acrylate, triallyl cyanurate, triallyl isocyanurate, triallyl phosphate, triallylamine, poly(meth)alllyloxyalkanes, (poly)ethylene glycol diglycidyl ether, glycerol diglycidyl ether, ethylene glycol, polyethylene glycol, propylene glycol, glycerol, pentaerythritol, ethylenediamine, polyethylenimine, and glycidyl(meth)acrylate. These crosslinking agents may be used either alone respectively or in combinations with each other. Among the above exemplifying compounds, those which have at least two polymerizable unsaturated groups are preferably used as the crosslinking agents.

The amount of the crosslinking agent as used is favorably in the range of 0.01 to 2 mol %, more favorably 0.03 to 0.2 mol %, of the total of the above-mentioned monomers. In the case where the amount of the crosslinking agent as used is smaller than 0.01 mol %, caution is needed, because it might be difficult to obtain the properties such as the suction power of not less than 9 g/g under a load by the below-mentioned surface-crosslinking treatment.

In addition, usable when the above polymerization is initiated are, for example, as follows: radical polymerization initiators such as potassium persulfate, ammonium persulfate, sodium persulfate, t-butyl hydroperoxide, hydrogen peroxide, and 2,2'-azobis(2-amidinopropane) dihydrochloride; or active energy rays such as ultraviolet rays and electron beams. In addition, when oxidizable radical polymerization initiators are used, redox polymerization can, for example, be carried out using jointly therewith reducing agents such as sodium sulfite, sodium hydrogensulfite, ferrous sulfate, and L-ascorbic acid. The amount of these polymerization initiators as used is favorably in the range of 0.001 to 2 mol %, more favorably 0.01 to 0.5 mol %.

In addition, also favorable is a way in which such as foaming agents (e.g. carbonate salts, azo compounds) or inert gases are added into the monomer during the polymerization in order for the resultant water-absorbent resin to have a porous structure, therefore, an increased specific surface area.

In addition, as to the process for producing the water-absorbent resin in the present invention, for example, in cases of aqueous solution polymerization, the process includes the following sequential steps of: arrangement of aqueous monomer solution—polymerization—fine particulation of polymer—drying—pulverization—classification.

In the case where the above aqueous solution polymerization is carried out, an aqueous monomer solution having a concentration of generally 10 weight % to saturation, favorably 20 to 60 weight %, is arranged and then polymerized. As to the polymerization method, examples thereof include: a method in which the polymerization is carried out in a twin-arm kneader while agitation is carried out if necessary; a method in which cast polymerization is carried out in a container; and a method in which static polymerization is (continuously) carried out on a moving belt.

For drying the polymer (hydrogel) resultant from the above polymerization step, it is desirable to finely particulate this hydrogel into predetermined particle diameters. The fine particulation of the hydrogel can be carried out during the polymerization by doing the polymerization under stirred conditions with such as twin-arm kneaders, or can be carried out by extruding the gel from dies with such as meat choppers after the polymerization. In addition, the fine particulation can also be carried out with such as cutting mills. The particle diameters of the finely particulated gel can fitly be set according to such as ability of driers, but is generally preferably in the range of 0.1 to 10 mm. In the case where the gel is finer than 0.1 mm, the properties of the resultant water-absorbent resin might be inferior. In the case where the gel is coarser than 10 mm, the gel might be difficult to dry.

In the fine particulation step, a coarse gel with particle diameters larger than 10 mm and a fine gel with particle diameters smaller than 0.1 mm might form. These polymers can be separated and then added to such as an aqueous monomer solution or a polymer gel.

The gel as finely particulated in the above fine particulation step is dried in the drying step. Examples of usable means for drying include hot-air driers, air blow type (pneumatic type) driers, azeotropic dehydration, fluidized-bed driers, drum driers, microwaves, and far infrared rays. The drying temperature is favorably not lower than 80° C., more favorably not lower than 120° C., still more favorably in the range of 150 to 250° C., yet still more favorably in the range of 160 to 220° C.

The above-mentioned water-absorbent resin may be granulated into a predetermined shape and can have various shapes such as spheres, scales, irregular pulverized shapes, and granules. Furthermore, the water-absorbent resin may comprise either substantially ungranulated primary particles or a granulated matter thereof.

The above-mentioned water-absorbent resin generally does not satisfy the requirements of the present invention for the ranges of the absorption capacity, the suction power under a load, and the water absorption rate. Therefore, the crosslinking density in the vicinity of surfaces of the water-absorbent resin needs to be rendered higher than that inside the water-absorbent resin by further using a crosslinking agent. In other words, water absorbent resins usable in the present invention are obtained by crosslinking the vicinity of surfaces of the water-absorbent resin with the crosslinking agent.

In the present invention, obtainable from these water-absorbent resins are a water-absorbent resin of which a surface portion and/or its vicinity is treated by crosslinking, and/or a water-absorbent resin which exhibits an absorption capacity of 25 to 60 g/g, a suction power of not less than 9 g/g under a load, and a water absorption rate of not more than 60 seconds.

Thus, the water-absorbent resin, according to the present invention, is favorably obtained by a process including the step of thermally treating the foregoing water-absorbent resin in the presence of the crosslinking agent reactable with a functional group of the water-absorbent resin (hereinafter such a crosslinking agent is referred to as surface-crosslinking agent) wherein the foregoing water-absorbent resin is a water-absorbent resin as obtained by the aqueous solution polymerization or reversed-phase suspension polymerization, favorably the aqueous solution polymerization, that is, a water-absorbent resin as obtained by making arrangements involving the operations such as polymerization and classification so that the weight-average particle diameter may be in the range of 100 to 600 μm, more favorably 200 to 500 μm, and that the proportion of particles having particle diameters of smaller than 106 μm may not be more than 10 weight %, favorably not more than 5 weight %, more favorably not more than 3 weight %.

The above surface-crosslinking agent is what has a functional group reactable with a functional group, such as acid group, of the water-absorbent resin, and examples thereof include conventional crosslinking agents which are usually used for the corresponding purpose.

In the case where the functional group of the water-absorbent resin is for example a carboxyl group, examples of the surface-crosslinking agent include one or more members selected from the group consisting of: polyhydric alcohol compounds such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, 2-butene-1,4-diol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol and sorbitol; epoxy compounds such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether and glycidol; polyamine compounds such as ethylenediamine, diethylenetriamine, triethylenetetramine, tetraethylenepentamine, pentaethylenehexamine, polyallylamine, and polyethylenimine; polyisocyanate compounds such as 2,4-tolylene diisocyanate and hexamethylene diisocyanate; polyoxazoline compounds such as 1,2-ethylenebisoxazoline; alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxopan-2-one; mono-, di-, or polyoxazolidine compounds; haloepoxy compounds such as epichlorohydrin, epibromohydrin and α-methylepichlorohydrin; polyvalent metallic compounds such as hydroxides and chlorides of such as zinc, calcium, magnesium, aluminum, iron and zirconium; silane coupling agents such as γ-glycidoxypropyltrimethoxysilane and γ-aminopropyltriethoxysilane; and polyamide-polyamine-epihalohydrin resins. Preferable are those which include at least one member selected from the group consisting of the polyhydric alcohol compounds, the polyamine compounds, the polyepoxy compounds, and the alkylene carbonate compounds.

The amount of the surface-crosslinking agent as used depends on factors such as the compounds as used as the surface-crosslinking agents or combinations of such compounds, but is favorably in the range of 0.001 to 5 weight parts, more favorably 0.01 to 1 weight part, per 100 weight parts of the solid content of the water-absorbent resin. If the above-mentioned surface-crosslinking agents are used, the crosslinking density in the vicinity of surfaces of the water-absorbent resin can be rendered higher than that inside, thereby forming what has the absorption properties which are required of the present invention resin. The amount larger than 10 weight parts of the surface-crosslinking agent as used is not only uneconomical, but also might be so excessive to the formation of the optimal crosslinked structure in the water absorbent resin as to unfavorably result in a low absorption capacity. In addition, in the case where the amount of the surface-crosslinking agent as used is smaller than 0.001 weight part, the suction power of the water-absorbent resin under a load might be difficult to enhance.

When the water-absorbent resin and the surface-crosslinking agent are mixed together, water is preferably used as a solvent. The amount of water as used depends upon such as type or particle diameters of the water-absorbent resin, but is favorably in the range of 0 to 20 weight parts (but not including 0 weight part), more favorably in the range of 0.1 to 10 weight parts, per 100 weight parts of the solid content of the water-absorbent resin.

In addition, when the water-absorbent resin and the surface-crosslinking agent are mixed together, a hydrophilic organic solvent may be used as a solvent, if necessary. Examples of the above hydrophilic organic solvent include: lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane and tetrahydrofuran; amides such as N,N-dimethylformamide; and sulfoxides such as dimethyl sulfoxide. The amount of the hydrophilic organic solvent as used depends upon such as type or particle diameters of the water absorbent resin, but is favorably not larger than 20 weight parts, more favorably not larger than 10 weight parts, per 100 weight parts of the solid content of the water-absorbent resin.

Examples of methods for mixing the water-absorbent resin and the surface-crosslinking agent together include a method comprising the steps of dispersing the water-absorbent resin into the above hydrophilic organic solvent, and then mixing the resultant dispersion with the surface-crosslinking agent. However, the mixing method is not especially limited. Preferable among various mixing methods is a method comprising the step of spraying or dropwise adding the surface-crosslinking agent (as dissolved in water and/or the hydrophilic organic solvent, if necessary) directly onto the water-absorbent resin, thus mixing them. In addition, in the case where the mixing step is carried out using water, there may coexist such as water-insoluble finely-particulate powders or surfactants.

A mixing apparatus, as used to mix the water-absorbent resin and the surface-crosslinking agent together, favorably has great mixing power to homogeneously and surely mix them. Preferable examples of the mixing apparatus include cylinder type mixers, double-wall cone type mixers, V-character-shaped mixers, ribbon type mixers, screw type mixers, fluidized type rotary disk type mixers, air blow type (pneumatic type) mixers, twin-arm kneaders, internal mixers, pulverizing type kneaders, rotary mixers, and screw type extruders.

Carrying out a thermal treatment, after mixing the water-absorbent resin precursor and the surface-crosslinking agent together, is favorable for obtaining the water-absorbent resin as used in the present invention, specifically, the water-absorbent resin of which a surface portion and/or its vicinity is treated by crosslinking with a crosslinking agent reactable with a functional group of the water-absorbent resin, and/or which exhibits an absorption capacity of 25 to 60 g/g, a suction power of not less than 9 g/g under a load, and an absorption rate of not more than 60 seconds. The treatment temperature in this thermal treatment depends upon the surface-crosslinking agent as used, but is favorably in the range of 40 to 250° C., more favorably 90 to 210° C. In the case where the treatment temperature is lower than 40° C., no uniform crosslinked structure is formed and it might therefore be impossible to obtain the water-absorbent resin of which the suction power under a load is in the range as defined by the present invention. In the case where the treatment temperature is higher than 250° C., caution is needed, because the water-absorbent resin might be degraded so much as to merely exhibit low performance.

The above thermal treatment can be carried out with conventional driers or heating furnaces.

Examples of the driers include channel type mixing driers, rotary driers, disk driers, fluidized-bed driers, air blow type (pneumatic type) driers, and infrared driers.

For obtaining the water-absorbent resin usable in the present invention, it is favorable to control such as crosslinking agent, mixing method, heating temperature, and treatment time, as mentioned above, so that the suction power under a load may not be less than 9 g/g.

The particulate water-absorbing composition, according to the present invention, is obtained by the process including the step of adding the plant powder to the water-absorbent resin of which a surface portion and/or its vicinity is favorably surface-treated with a crosslinking agent, and/or to the water-absorbent resin which resin exhibits an absorption capacity of 25 to 60 g/g, favorably not less than 27 g/g, more favorably not less than 29 g/g, still more favorably not less than 31 g/g, a suction power of not less than 9 g/g, favorably not less than 10 g/g, more favorably not less than 11 g/g, under a load, and an absorption rate of not more than 60 seconds, favorably not more than 55 seconds, more favorably not more than 50 seconds, wherein these water-absorbent resins are obtained in the above ways.

A plant powder usable in the present invention comprises a powder of a Tracheophyta (Spermatophyta, Pteridophyta) plant, a Bryophyta plant, or algae, favorably, the powder of the Tracheophyta plant.

The plant powder usable in the present invention may be a product obtained by a process including the step of pulverizing a plant residue which is formed as a by-product in production processes in plant- and food-processing industries if such a plant powder satisfies the performance as required in the present invention.

It is also a favorable mode that the plant powder usable in the present invention comprises a spice, and further it is yet also a favorable mode that the plant powder usable in the present invention comprises a tea leaf and/or a residue of extraction therefrom.

In the present invention, there is no especial limitation with regard to portions being used of plants used as the plant powder if they satisfy the performance as required in the present invention. Such a portion is, for example, at least one portion selected from the group consisting of such as leaves, branches, trunks, stalks, roots, fruits, flowers, seeds, and barks.

The particle size of the plant powder usable in the present invention is such that the plant powder can pass through a mesh of which the mesh opening size is 850 μm, favorably 600 μm, more favorably 500 μm, still more favorably 300 μm.

That is to say, the plant powder usable in the present invention is such that in the case where such a plant powder as passes through the mesh having the mesh opening size of 850 μm is used for the particulate water-absorbing composition, this particulate water-absorbing composition can, as is mentioned below, exhibit an offensive-odor removal index of not less than 180 wherein the offensive-odor removal index is represented by the following equation:

offensive-odor removal index=1.1×hydrogen sulfide removal ratio+2.0×methylmercaptan removal ratio+0.3×ammonia removal ratio.

The aspect ratio of the plant powder usable in the present invention (which is a value as calculated from the following equation: aspect ratio=length/breadth wherein the length and the breadth are those of the plant powder) is favorably in the range of 1 to 50 (but not including 50), more favorably 1 to 40 (but not including 40), still more favorably 1 to 30 (but not including 30).

The water content of the plant powder usable in the present invention is not especially limited, but is favorably not more than 40%, more favorably not more than 30%, still more favorably not more than 20%, yet still more favorably not more than 10%.

In the case where the plant powder usable in the present invention comprises the powder of the Tracheophyta plant, this Tracheophyta plant is favorably at least one kind of Tracheophyta plant selected from the group consisting of Gramineae, maple family, Ebenaceae, Betulaceae, Compositae, Lamiaceae, cryptomeria family, Umbelliferae, Rosaceae, Vitaceae, Japanese cypress family, pine family, Fagaceae, Brassicaceae, Leguminosae, Rutaceae, Cucurbitaceae, Solanaceae, Piperaceae, Zingiberaceae, Lauraceae, Malvaceae, and Theaceae.

Examples of the Tracheophyta plant on the Gramineae include rice plants, bamboo grasses, bamboos, maize, barley and wheat. Examples of the Tracheophyta plant on the maple family include maples. Examples of the Tracheophyta plant on the Ebenaceae include persimmons. Examples of the Tracheophyta plant on the Betulaceae include hornbeams, hazels, birches, and alders. Examples of the Tracheophyta plant on the Compositae include chrysanthemums, burdocks, dandelions, and mugworts. Examples of the Tracheophyta plant on the Lamiaceae include Utsubogusa (in Japanese) (herein the italics with "(in Japanese)" are as they are original Japanese words, because no proper English equivalents therefor are found), Egoma (in Japanese), Odorikoso (in Japanese), perillas, and peppermint. Examples of the Tracheophyta plant on the cryptomeria family include cryptomerias, China-Firs, and Taiwanese cryptomerias. Examples of the Tracheophyta plant on the Umbelliferae include umbelliferous plants resembling stone parsley used in cooking for their aroma (mitsuba in Japanese), carrots, parsley, and celery. Examples of the Tracheophyta plant on the Rosaceae include Japanese apricots (ume in Japanese), cherries, spireas, roses, apricots, pears, peaches, apples, strawberries, plums, hawthorns, loquats, raphiolepises, Japanese quinces, Kamatsuka (in Japanese) (Pourthiaea), mountain ashes, and kerrias. Examples of the Tracheophyta plant on the Vitaceae include grapes, ivy, and wild grapes. Examples of the Tracheophyta plant on the Japanese cypress family include Japanese cypresses, arbor-vitaes, hiba arbor-vitaes, junipers, and sawara (in Japanese) cypresses (*Chamaecyparis pisifera*). Examples of the Tracheophyta plant on the pine family include larches, hemlock spruces, spruces, pines, firs, and Himalayan cedars. Examples of the Tracheophyta plant on the Fagaceae include beeches, chestnuts, chinquapins, shirakashi (in Japanese) (*Quercus myrsinaefolia*), arakashi (in Japanese) (*Quercus glauca*), and urazirogashi (in Japanese) (*Quercus salicina*). Examples of the Tracheophyta plant on the Brassicaceac include Japanese white radishes and rape. Examples of the Tracheophyta plant on the Leguminosae include adzuki, licorice, broad beans, and soybeans. Examples of the Tracheophyta plant on the Rutaceae include mandarins (mandarin oranges), oranges, grapefruits, shaddocks, Japanese pepper trees, citrons, lemons, and limes. Examples of the Tracheophyta plant on the Cucurbitaceae include pumpkins, cucumbers, watermelons, loofahs, and bottle gourds. Examples of the Tracheophyta plant on the Solanaceae include eggplants, capsicums, green peppers, and tomatoes. Examples of the Tracheophyta plant on the Piperaceae include peppers. Examples of the Tracheophyta plant on the Zingiberaceae include ginger. Examples of the Tracheophyta plant on the Lauraceae include camphor trees, camphor, spice bushes, shiromoji (in Japanese) (Parabenzoin), laurels, shirodamo (in Japanese) (Neolitsea), and hamahiwa (in Japanese) (*Litsea*). Examples of the Tracheophyta plant on the Malvaceae include hollyhocks, mallows, rose mallows, hibiscuses, kan-aoi (in Japanese), and kenafs. Examples of the Tracheophyta plant on the Theaceae include camellias, scarlet sakaki (in Japanese) plants, sakaki (in Japanese) plants, and mokkoku (in Japanese) (*Ternstroemia*).

The spice usable in the present invention is such that seeds, fruits, buds, leaves, barks, or rhizomes of spice plants are dried and then, either intactly or after powdering, used to get them to serve as a seasoning or condiment for foods. So many spices are used for foods, and the spice is produced naturally or by culture. The usable spice means a product obtained using a spice as a starting material, which product is, for example, a spice produced by intactly arranging the shape or particles of its starting material, or a spice powder formed by pulverizing its starting material. The usable spice is not such as is obtained by separating only a single component from a spice, but such as contains various components.

The spice favorably usable in the present invention is a spice having deodorizability, and is not especially limited, but can be exemplified by Tracheophyta plants such as ajowan, anises, fennels, turmeric, allspices, oreganos, mustard, cardamoms, caraways, cumin, cloves, peppers, corianders, saffron, Japanese peppers, perillas, cinnamons, ginger, cardamoms, ziiru (in Japanese), star anises, sage, onions, thyme, turmeric, cloves, dill, capsicums, nutmegs, nikuzuku (in Japanese) (nutmegs), garlic, peppermint, parsley, basil, paprika, vanillas, feneguriiku (in Japanese), fennels, mace, rosemary, laurier, laurels, and Japanese horseradishes. Of these spices, particularly, those which exhibit the deodorizability without the masking-like function are used favorably for providing the deodorizability without giving wearers an unpleasant feeling in the case of uses for absorbent articles. Above all, peppers, Japanese peppers, ginger, capsicums, parsley, and Japanese horseradishes are used especially favorably for the present invention.

The shape of the above spices is different according to the aimed deodorizability, but is powdery, and the size of their particles is such that they can pass through a mesh of which the mesh opening size is 850 μm, favorably 600 μm, more favorably 500 μm, still more favorably 300 μm, and further that the volume-average particle diameter is favorably not larger than 850 μm, more favorably not larger than 600 μm, still more favorably not larger than 500 μm, yet still more favorably not larger than 300 μm. Common liquid spices are unfavorable, because they might be so aromatic as to give an unpleasant feeling. In addition, in the case where the particle diameter is larger than 850 μm, the actions of effective components contained in the spice might unfavorably be insufficient to provide stable deodorizability during contact with urine. In addition, it is preferable that the volume-average particle diameter of the spice is smaller than the weight-average particle diameter of the water-absorbent resin, because more excellent deodorizability can be provided in such a case.

The water content of the spice usable in the present invention is not especially limited, but is favorably not more than 40%, more favorably not more than 30%, still more favorably not more than 20%, yet still more favorably not more than 10%.

The tea leaf usable in the present invention is such as obtained by processing a plant which is a Tracheophyta plant so that it may be fit to drink. Examples thereof include agarisk tea, ashitaba-cha (in Japanese), hydrangea vine tea, aloe tea, ginkgo leaf tea, Araliaceae tea, turmeric tea, urazirogashi-cha (in Japanese) (*Quercus stenophylla* tea), oolong tea, plantain tea, persimmon leaf tea, licorice tea, chrysanthemum tea, gymnema tea, Chinese matrimony vine tea, low striped bamboo tea, cranesbill tea, black tea, hawthorn tea, perillas tea, jasmine tea, sugina-cha (in Japanese), senna tea, mulberry leaf tea, buckwheat tea, tahibo-cha (in Japanese), dandelion tea, Chinese tea, tetsukannon-cha (in Japanese), ten-cha (in Japanese), tochu-cha (in Japanese), dokudami-cha (in Japanese), shepherd's purse tea, nandin tea, basera-cha (in Japanese), Banaba (Lagerstoemia Speciosa Pers) tea, adlay tea, loquat tea, Pu-erh tea, pine needle tea, parched barley tea, mugwort tea, green tea, gentian tea, and Rooibos tea, and, preferably, those which are obtained by processing evergreen low trees on the Theaceae and their leaves so that they may be fit to drink, such as green tea, black tea, and oolong tea.

The general value of the water content in the above tea leaf is, for example, in the range of 6 to 9 g per 100 g of the tea leaf, but the water content of the tea leaf as used in the present invention is not especially limited, but tea leaves having various water contents are usable.

The residue of extraction from the tea leaf, usable in the present invention, can be exemplified by residues of extraction from the above tea leaves, and, favorably, a dried product of the residue of extraction from the tea leaf is used. What is referred to as the dried product of the residue of extraction from the tea leaf in the present invention is an extraction residue which is left behind in extraction of tea from the above tea leaf, and is a substantially dry one, of which the water content is not more than 40%, favorably not more than 30%, more favorably not more than 20%, still more favorably not more than 10%. Having water contents in these ranges is favorable also for facilitation of handling of the extraction residue.

Fine powders which are formed as by-products in processes for production of tea, or tea leaves and/or residues of extraction therefrom which are discharged as the extraction residues being left behind in extraction of tea, are presently disposed of, and are therefore utilizable favorably in aspects of such as effective utilization of resources or prices.

The shape of the above tea leaf and/or residue of extraction therefrom is different according to the aimed deodorizability, but is powdery, and the size of their particles is such that they can pass through a mesh of which the mesh opening size is 850 μm, favorably 600 μm, more favorably 500 μm, still more favorably 300 μm. The volume-average particle diameter is favorably not larger than 500 μm, more favorably not larger than 300 μm. In the case where the volume-average particle diameter is larger than 500 μm, the actions of effective components contained in the tea leaf and/or residue of extraction therefrom might unfavorably be insufficient to provide stable deodorizability during contact with urine. In addition, it is preferable that the volume-average particle diameter of the tea leaf and/or residue of extraction therefrom is smaller than the weight-average particle diameter of the water-absorbent resin, because more excellent deodorizability can be provided in such a case.

As to absorbent articles (such as diapers) in which conventional water-absorbent resins containing the above plant powder are used, some of those water-absorbent resins might provide the deodorizability to the whole diaper so insufficiently as to give wearers an unpleasant feeling. However, the particulate water-absorbing composition according to the present invention solves the above problems by specifying the properties of a water-absorbent resin which has not yet been mixed with the plant powder, and this particulate water-absorbing composition can provide excellent deodorizability and excellent absorption properties to absorbent articles and is favorably used for the absorbent articles.

In addition, as to conventional water-absorbent resins, the balance between their water absorption properties is being improved by subjecting a surface portion and/or its vicinity of the water-absorbent resin to a crosslinking treatment with a crosslinking agent reactable with a functional group of the water-absorbent resin, but, in the case where the water-absorbent resin is used in absorbent articles (such as diapers), the water-absorbent resin might deteriorate with the passage of time so much as to provide inferior results with regard to the liquid permeability, gel strength, or absorption properties. However, because of containing the plant powder, the particulate water-absorbing composition according to the present invention is surprisingly a particulate water-absorbing composition which deteriorates little with the passage of time after absorption of urine and exhibits excellent gel stability, and can provide excellent deodorizability and excellent absorption properties to absorbent articles for a long time and is favorably used for the absorbent articles.

The amount of the above plant powder as used is different according to the aimed deodorizability, but the amount thereof as added is favorably in the range of 0.001 to 20 weight parts, more favorably 0.01 to 10 weight parts, still more favorably 0.01 to 5 weight parts, per 100 weight parts of the solid content of the water-absorbent resin.

In addition, examples of methods for adding the above plant powder include: a method comprising the step of mixing the water-absorbent resin directly with the plant powder so that a desired amount of the plant powder may be added to the water-absorbent resin (for example, a dry blend method in which powders are mixed together); a method comprising the steps of mixing the water-absorbent resin directly with the plant powder, and then spraying or dropwise adding such as water, aqueous liquids, or various organic solvents onto the resultant mixture, thus mixing them; and a method comprising the steps of dispersing the plant powder into such as water, aqueous liquids, or various organic solvents, and then spraying or dropwise adding the resultant dispersion directly onto the water-absorbent resin, thus mixing them. Incidentally, there can also be adopted the following methods: a method comprising the step of adding the plant powder during the polymerization of the water-absorbent resin; and a method comprising the step of adding the plant powder to the resultant gel after the polymerization. However, in cases where these methods are adopted, they need to be carried out in a way such that the resultant composition will satisfy the claimed ranges of the absorption capacity, the suction power under a load, and the absorption rate as a result of the steps as thereafter carried out.

Particularly preferable of the above methods for adding the plant powder are as follows: the method comprising the steps of mixing the water-absorbent resin directly with the plant powder, and then spraying or dropwise adding such as water, aqueous liquids, or various organic solvents onto the resultant mixture, thus mixing them; the method comprising the steps of dispersing the plant powder into such as water, aqueous liquids, or various organic solvents, and then spraying or dropwise adding the resultant dispersion directly onto the water-absorbent resin, thus mixing them; the method comprising the step of adding the plant powder during the polymerization of the water-absorbent resin; and the method comprising the step of adding the plant powder to the resultant gel after the polymerization. These methods give a form in which the plant powder is held by the water-absorbent resin.

As to the present invention, in the case where the water-absorbent resin and the plant powder are mixed together, the optimum amount of such as water, water vapor, or aqueous liquids including water and hydrophilic organic solvents, which are added if necessary, is different according to the type or particle diameters of the water-absorbent resin. However, in the case of water, the amount thereof is usually not larger than 10 weight parts, favorably in the range of 1 to 5 weight parts, per 100 weight parts of the solid content of the water-absorbent resin. In addition, similarly, the amount of the hydrophilic organic solvent as used is usually not larger than 10 weight parts, favorably in the range of 0.1 to 5 weight parts, per 100 weight parts of the solid content of the water-absorbent resin.

The apparatus which is used to mix the water absorbent resin and the plant powder together in the present invention may be a conventional one, and examples thereof include cylinder type mixers, screw type mixers, screw type extruders, turbilizers, Nauta type mixers, V-character-shaped mixers, ribbon type mixers, twin-arm kneaders, fluidizing type mixers, air blow type (pneumatic type) mixers, rotary disk type mixers, roll mixers, and tumbling type mixers. The mixing speed may be either high or low.

Various inorganic powders may be added further to the above water absorbent resin and/or particulate water-absorbing composition. Specific examples of the inorganic powder include: metal oxides such as silicon dioxide and titanium oxide; silicic acid (or its salts) such as natural zeolite and synthetic zeolite; kaolin; talc; clay; and bentonite. Among these, favorable ones are silicon dioxide and silicic acid (or its salts), and more favorable ones are silicon dioxide and silicic acid (or its salts) with an average particle diameter of not larger than 200 μm as measured by the Coulter Counter Method. The amount of the inorganic powder depends on combinations of the water-absorbent resin and/or particulate water-absorbing composition with the inorganic powder, but is in the range of 0.001 to 10 weight parts, favorably 0.01 to 5 weight parts, per 100 weight parts of the water absorbent resin and/or particulate water-absorbing composition. The method for mixing the water-absorbent resin and/or particulate water-absorbing composition with the inorganic powder is not especially limited, and, for example, dry blend methods in which powders are mixed together or wet mixing methods are available, but the dry blend methods are preferable.

Incidentally, a difference between the plant powder and a powder on which an essence extracted from a plant (essential oil) is carried is as follows: components having the deodorizing effect are retained in fibrous portions of the plant powder, and liquids such as urine prevent the deodorizing components from volatilizing and/or flowing out, and the deodorizing components effectively work as the need arises, and further, fibrous portions of plants seem to also have an effect on such as adsorption of malodorous components.

In addition, another difference between the plant powder and the powder on which the essence extracted from a plant (essential oil) is carried is as follows: the latter has a great powder odor strength and therefore displays a high deodorizing effect during the practical use, but this deodorizing effect is mainly from an odor-masking effect. The deodorization by masking is not suitable, because it involves smells peculiar to the masking material, and because there are differences between individuals' tastes for smells.

The powder odor strength is favorably not more than 4, more favorably not more than 3, still more favorably not more than 2, most favorably not more than 1.

The particulate water-absorbing composition as obtained by the above production process is a particulate water-absorbing composition which comprises a plant powder and a water-absorbent resin, wherein the water-absorbent resin is the specific water-absorbent resin, namely, the water-absorbent resin of which a surface portion and/or its vicinity is treated by crosslinking with a crosslinking agent reactable with a functional group of the water-absorbent resin, and/or which exhibits an absorption capacity of 25 to 60 g/g, a suction power of not less than 9 g/g under a load, and an absorption rate of not more than 60 seconds.

A particulate water-absorbing composition, according to the present invention, is characterized by comprising a plant powder and a water-absorbent resin, wherein the water-absorbent resin is the specific water-absorbent resin, namely, the water-absorbent resin of which a surface portion and/or its vicinity is treated by crosslinking with a crosslinking agent reactable with a functional group of the water-absorbent resin, and/or which exhibits an absorption capacity of 25 to 60 g/g, a suction power of not less than 9 g/g under a load, and an absorption rate of not more than 60 seconds, and wherein the particulate water-absorbing composition exhibits an offensive-odor removal index of not less than 180 wherein the offensive-odor removal index is represented by the following equation:

$$\text{offensive-odor removal index} = 1.1 \times \text{hydrogen sulfide removal ratio} + 2.0 \times \text{methylmercaptan removal ratio} + 0.3 \times \text{ammonia removal ratio}.$$

As is mentioned below, the offensive-odor removal index is an index as calculated from the three removal ratios: hydrogen sulfide removal ratio, methylmercaptan removal ratio, and ammonia removal ratio; and it is needed for the particulate water-absorbing composition according to the present invention that this offensive-odor removal index is not less than 180.

JP-A-079159/2000 and JP-A-116829/1999 disclose the malodorous-substance removability of water-absorbent resins and their deodorizing effect during their practical use. As to JP-A-079159/2000, ammonia is used as the malodorous substance, but, actually, malodorous components of liquids (e.g. urine, menstrual blood) as excreted out of bodies are so various that it does not follow that the ammonia removability copes with all odors. In addition, as to JP-A-116829/1999, the deodorizing effect of water-absorbent resins is examined in a liquid-unabsorbed (unswollen) state by using ammonia, methylamine, and t-butylmercaptan as the malodorous substances to measure their concentrations remaining after a predetermined time has passed, and further the deodorizing effect of water-absorbent resins is further examined by using human urine as an evaluation close to a practical state of the use of absorbent articles to measure the concentrations of gases of ammonia, methylamine, hydrogen sulfide, and methylmercaptan after a predetermined time has passed. However, the removal effect on these malodorous components is different from the human sense of smell and, therefore, even if the offensive odors are much removed, there cannot be said to be the effect in cases of the practical use.

In addition, as to the measurement of the removal of already known malodorous substances, the results thereof are much different according to measurement conditions such as concentrations of the malodorous substances, time passing until the measurement, temperature in a period of until the measurement, and amounts of water-absorbent resins as used.

Thus, the present inventors diligently studied about water-absorbent resins having the deodorizing effect during the practical use. As a result, it is not until by the present inventors that the particulate water-absorbing composition comprising the water-absorbent resin and the plant powder and displaying the offensive-odor removability (herein referred to as offensive-odor removal index) under specific conditions has been found out to display the effect also during the practical use, wherein the water-absorbent resin is the specific water-absorbent resin, namely, the water-absorbent resin of which a surface portion and/or its vicinity is treated by crosslinking with a crosslinking agent reactable with a functional group of the water-absorbent resin, and/or which exhibits an absorption capacity of 25 to 60 g/g, a suction power of not less than 9 g/g under a load, and an absorption rate of not more than 60 seconds.

The offensive-odor removal index is an total expression of the ratios of removals of ammonia, methylmercaptan, and hydrogen sulfide as the malodorous components by the above particulate water-absorbing composition under specific conditions and is represented by the following relational formula:

$$\text{offensive-odor removal index} = 1.1 \times \text{hydrogen sulfide removal ratio} + 2.0 \times \text{methylmercaptan removal ratio} + 0.3 \times \text{ammonia removal ratio}.$$

Thus, it is not until by setting the degree of importance upon the ratios of removals of the malodorous components by the particulate water-absorbing composition comprising the water-absorbent resin and the plant powder that it has become possible to quantify the human sense of smell to offensive odors.

However, the above relational formula according to the present invention is related only to the particulate water-absorbing composition comprising the water-absorbent resin and the plant powder, and it is not until by the present inventors that the particulate water-absorbing composition has been found out to display the effect during the practical use in the case where the offensive-odor removal index of this composition is not less than 180.

Incidentally, in general, particulate water-absorbing compositions which satisfy the offensive-odor removal index of not less than 180 do not necessarily display the effect upon liquids (e.g. urine, menstrual blood) as excreted out of bodies. The reason for this can be considered to be that the offensive-odor removability (removability upon various malodorous components contained in liquids as excreted out of bodies), during the practical use, of the particulate water-absorbing composition comprising the water-absorbent resin and the plant powder can be simulated by the aforementioned relational formula dealing with ammonia, methylmercaptan, and hydrogen sulfide.

The offensive-odor removal index is favorably not less than 200, more favorably not less than 220, still more favorably not less than 240, yet still more favorably not less than 260, particularly favorably not less than 280. In the case where the offensive-odor removal index is less than 180, there are disadvantages in that the effects of the present invention cannot sufficiently be displayed.

If the water-absorbent resin and/or the plant powder is selected to enhance the offensive-odor removal index of the particulate water-absorbing composition, then it is possible to obtain a particulate water-absorbing composition which displays a still higher deodorizing effect during the practical use.

The particulate water-absorbing composition, according to the present invention, preferably exhibits an absorption capacity of 25 to 60 g/g, a suction index of not less than 14 g/g under a load, and an absorption rate of not more than 60 seconds.

The above absorption capacity is more favorably not less than 27 g/g, still more favorably not less than 29 g/g, particularly favorably not less than 31 g/g. In the case where the absorption capacity is less than 25 g/g, there are disadvantages in that the absorption quantity is insufficient. In the case where the absorption capacity is more than 60 g/g, there are disadvantages in that the gel strength is so weak that the gel blocking easily occurs.

The above suction index under a load is a new parameter for measuring the power for the water-absorbent resin to suck liquids from paper, and is represented by the sum of a value displayed for a liquid absorption time of 3 minutes and a value displayed for a liquid absorption time of 60 minutes. If this total value is high, the power to suck liquids surrounding the particulate water-absorbing composition is so great as to serve to enhance the deodorizing effect of the plant powder by taking in liquids (e.g. urine, menstrual blood) which are excreted out of bodies to emit offensive odors. In addition, such a function provides the excellent deodorizing effect not only to the particulate water-absorbing composition, but also to absorbent articles. The suction index under a load is more favorably not less than 16 g/g, still more favorably not less than 18 g/g, particularly favorably not less than 20 g/g.

The above absorption rate is more favorably not more than 55 seconds, still more favorably not more than 50 seconds. In the case where the absorption rate is more than 60 seconds, there are disadvantages in that the liquid absorption is slow and that the deodorizing effect is also deteriorated.

The above absorption properties, represented by the absorption capacity, the suction index under a load, and the absorption rate, can not only enhance the deodorizing function, but also provide actual absorbent articles with the reduction of leakage, the reduction of the desorption (wet back) quantity, the prevention of a buttock rash, and the enhancement of a dryness feeling.

With regard to the particulate water-absorbing composition according to the present invention, the weight-average particle diameter is favorably in the range of 100 to 600 μm, more favorably 200 to 500 μm, and the proportion of particles having particle diameters of smaller than 106 μm is favorably not more than 10 weight %, more favorably not more than 5 weight %, still more favorably not more than 3 weight %.

The particulate water-absorbing composition, according to the present invention, is favorably used for sanitary materials.

The absorbent article, according to the present invention, comprises an absorbent layer, a liquid-permeable surface sheet, and a liquid-impermeable back sheet, wherein the absorbent layer includes the present invention particulate water-absorbing composition.

As to the absorbent article according to the present invention, favorably the weight ratio of the particulate water-absorbing composition as included in the absorbent layer is not less than 0.3. Favorably the weight ratio of the particulate water-absorbing composition to the total of hydrophilic fibers and the particulate water-absorbing composition is not less than 0.3. Such a weight ratio is more favorably in the range of 0.4 to 1.0, still more favorably 0.5 to 0.8.

As to the absorbent article according to the present invention, in the case where the weight ratio of the particulate water-absorbing composition as included in the absorbent layer is less than 0.3, there are disadvantages in that the amount of the particulate water-absorbing composition as used might be too small to sufficiently provide the deodorizability to the whole diaper.

The water-absorbent resin which is a component of the particulate water-absorbing composition as included in the absorbent layer of the absorbent article according to the present invention comprises a crosslinked poly(acrylic acid (salt)) as the main component.

The particulate water-absorbing composition as included in the absorbent layer of the absorbent article according to the present invention is a particulate water-absorbing composition according to the present invention, and is therefore characterized by exhibiting an offensive-odor removal index of not less than 180 which is represented by the following equation:

offensive-odor removal index=1.1×hydrogen sulfide removal ratio+2.0×methylmercaptan removal ratio+0.3×ammonia removal ratio.

Furthermore, the particulate water-absorbing composition, as included in the absorbent layer of the absorbent article according to the present invention, favorably exhibits an absorption capacity of 25 to 60 g/g, a suction index of not less than 14 g/g under a load, and an absorption rate of not more than 60 seconds, wherein the absorption capacity is more favorably not less than 27 g/g, still more favorably not less than 29 g/g, particularly favorably not less than 31 g/g, and wherein the suction index under a load is more favorably not less than 16 g/g, still more favorably not less than 18 g/g, particularly favorably not less than 20 g/g, and wherein the absorption rate is more favorably not more than 55 seconds, still more favorably not more than 50 seconds.

Furthermore, the particulate water-absorbing composition, as included in the absorbent layer of the absorbent article according to the present invention, favorably exhibits a color-difference (L, a, b) in which: L is not less than 40; the absolute value of a is not more than 6; and b is in the range of 0 to 15; wherein L is more favorably not less than 50; still more favorably not less than 60, and wherein the absolute value of a is more favorably not more than 5; still more favorably not more than 4, and wherein b is more favorably in the range of 0 to 14; still more favorably 0 to 13. A color-difference deviating from the above ranges has the disadvantage of being recognized as a foreign substance by consumers in the case of being used for diapers.

As to the absorbent article according to the present invention, the above modes are favorable, but one of particularly favorable modes is an absorbent article which comprises an absorbent layer, a liquid-permeable surface sheet, and a liquid-impermeable back sheet, wherein the absorbent layer includes an absorbent structure such that the weight ratio of the particulate water-absorbing composition to the total of hydrophilic fibers and the particulate water-absorbing composition is not less than 0.3, and which is characterized in that the particulate water-absorbing composition includes a water-absorbent resin comprising a crosslinked poly(acrylic acid (salt)) as the main component and has the following properties:

an offensive-odor removal index of not less than 180;
a suction index of not less than 14 under a load;
a color-difference (L, a, b) in which: L is not less than 40; the absolute value of a is not more than 6; and b is in the range of 0 to 15;
an absorption capacity of 25 to 60 g/g; and
an absorption rate of not more than 60 seconds.

In a process for producing this absorbent article, for example, the particulate water-absorbing composition is blended or sandwiched with a fibrous material to prepare an absorbent layer (absorbent core), and the resultant absorbent core is sandwiched between a liquid-permeable base material (surface sheet) and a liquid-impermeable base material (back sheet), and the resultant product is, if necessary, provided with materials such as an elastic member, a diffusion layer, or a pressure sensitive adhesive tape, thus obtaining an absorbent article, particularly, a disposable diaper for adults or a sanitary napkin. The above absorbent core is, for example, subjected to compression forming so as to have a density of 0.06 to 0.50 g/cc and a basis weight of 0.01 to 0.20 g/cm$^2$. Incidentally, examples of usable fibrous materials include hydrophilic fibers such as pulverized wood pulp, and other examples include cotton linters, crosslinked cellulose fibers, rayon, wadding, wool, acetate, and vinylon. Preferably, they may be air-laid.

Favorable examples of the above hydrophilic fibers include mechanically pulverized wood pulp, chemical pulp, kraft pulp, cotton, rayon, wadding, wool, acetate, vinylon, polyolefin fibers, and polyester fibers. These fibers may be used either alone respectively or in combination with each other so as to have such as laminate structures or core-sheath structures. Of the above fibers, those of which the surfaces are hydrophobic are subjected to hydrophilization treatment before being used.

In addition, hydrophilic fibers which are obtained from plants are fibrous, not powdery. It is generally a fine-thread-shaped substance that is referred to as "fibrous", and such a substance favorably has an aspect ratio value larger than the aspect ratio range of the plant fiber as referred to in the present invention. The aspect ratio is a value as calculated from the following equation: aspect ratio=length/breadth wherein the length and the breadth are those of the hydrophilic fiber.

As is aforementioned, the particulate water-absorbing composition according to the present invention can provide the deodorizing function to absorbent articles and exhibits excellent deodorizability and excellent absorption properties for a long time. Specific examples of such absorbent articles include sanitary materials such as disposable diapers for adults, which greatly develop in recent years, diapers for children, sanitary napkins, and so-called incontinent pads, but there is no especial limitation thereto. The particulate water-absorbing composition, as included in the absorbent article, has very excellent deodorizability and gel stability, and the absorbent article displays little desorption (wet back) and therefore gives a great dryness feeling, whereby the burden on wearers of the absorbent article or on people who take care of the wearers can greatly be lessened.

In addition, the absorbent structure, according to the present invention, comprises a hydrophilic fiber, a plant powder, and a water-absorbent resin; and is characterized by exhibiting an offensive-odor removal index of not less than 180 as a particulate water-absorbing composition including a mixture of the plant powder and the water-absorbent resin, wherein the offensive-odor removal index is represented by the following equation:

offensive-odor removal index=1.1×hydrogen sulfide removal ratio+2.0×methylmercaptan removal ratio+0.3×ammonia removal ratio.

The above wording "as a particulate water-absorbing composition including a mixture of the plant powder and the water-absorbent resin" means "as a particulate water-absorbing composition which is obtained in the case where the plant powder and the water-absorbent resin are mixed together in a weight ratio appropriate to the use for the absorbent structure".

As to the absorbent structure according to the present invention, the plant powder and the water-absorbent resin may separately be put into the absorbent structure. The absorbent structure, according to the present invention, favorably comprises the particulate water-absorbing composition in which the plant powder is held by the water-absorbent resin. Namely, it favorable that at least parts of the plant powder and the water-absorbent resin, which are included in the absorbent structure, are in the form where the plant powder is held by the water-absorbent resin.

BRIEF DESCRIPTION OF THE DRAWING

FIG. 1 is a schematic section of a measurement apparatus as used for measuring the suction power under a load, which is one of the properties as displayed by water-absorbent resins.

In FIG. 1, the symbol "1" represents a container, and the symbol "2" represents a filter paper, and the symbol "3" represents a measurement section, and the symbol "4" represents an artificial urine, and the symbol "5" represents a supporting cylinder, and the symbol "6" represents a metal gauze, and the symbol "7" represents a weight.

BEST MODE FOR CARRYING OUT THE INVENTION

Hereinafter, the present invention is more specifically illustrated by the following examples of some preferred embodiments in comparison with comparative examples not according to the invention. However the present invention is not limited to these examples. Incidentally, the various properties of water-absorbent resins and the volume-average particle diameter of plant powders were measured according to the following methods.

(a) Absorption Capacity

To a bag (60 mm×60 mm) made by nonwoven fabric, 0.2 g of water-absorbent resin (or particulate water-absorbing composition) was uniformly added, and then immersed in 100 g of aqueous sodium chloride solution of 0.9 weight % (physiological saline) of which the temperature had been adjusted to 25° C. The bag was pulled up after 60 minutes, and the weight (W2 (g)) of the bag was measured after removing water with a centrifugal separator (250 G) for 3 minutes. In addition, the same procedure was carried out without using the water-absorbent resin, and the resultant weight (W1 (g)) of the bag was measured. Then, the absorption capacity (g/g) of the water-absorbent resin was calculated from these weights W1 and W2 in accordance with the following equation:

$$\text{water absorption capacity (g/g)}=(\text{weight }W2\text{ (g)}-\text{weight }W1\text{ (g)})/0.2\text{ (g)}.$$

(b) Suction Power Under Load and Suction Index Under Load

First of all, the measurement apparatus as used for measuring the suction power under a load is hereinafter shortly explained while referring to FIG. 1.

As is shown in FIG. 1, the measurement apparatus comprises: a receptacle 1; filter paper 2 (No. 2, produced by Advantech, diameter=90 mm, ten pieces); and a measurement part 3.

The receptacle 1 contains 25 g of artificial urine 4 (of which the composition is as follows: 97.1 g of deionized water, 1.9 g of urea, 0.8 g of sodium chloride, 0.1 g of magnesium chloride hexahydrate, and 0.1 g of calcium chloride) wherein the temperature of the artificial urine is adjusted to 25° C.

The measurement part 3 has a supporting cylinder 5, a wire net 6, and a weight 7 wherein the wire net 6 is attached at the bottom of the supporting cylinder 5. Then, the measurement part 3 is formed by mounting the supporting cylinder 5 (namely, the wire net 6) on the filter paper 2 in this order, and further mounting the weight 7 inside the supporting cylinder 5, namely, on the wire net 6. The inner diameter of the supporting cylinder 5 is formed in 60 mm. The wire net 6 is made of stainless steel and formed in 400 mesh (mesh opening size: 38 μm). The total weight of the supporting cylinder 5 and the wire net 6 is adjusted to 62 g. Then, an arrangement is made such that a predetermined amount of water-absorbent resin (or particulate water-absorbing composition) can uniformly be spread on the wire net 6. The weight 7 is adjusted in weight such that a load of 1.96 kPa can uniformly be applied to the wire net 6, in other words, to the water-absorbent resin.

The suction power under a load and the suction index under a load were measured with the measurement apparatus having the above-mentioned constitution. The measurement methods are hereinafter explained.

(1) Suction Power Under Load

First of all, the filter paper 2 was mounted on the receptacle 1. Next, 25 g of the artificial urine 4 of which the temperature has been adjusted to 25° C. is added thereto so that the filter paper 2 will absorb it. On the other hand, in parallel with this mounting operation, 1.0 g of water-absorbent resin (or particulate water-absorbing composition) was uniformly spread inside the supporting cylinder 5, namely, on the wire net 6, and the weight 7 was put on this water-absorbent resin. Then, the weight of the supporting cylinder 5 including the water-absorbent resin and the weight 7 was measured (as weight W1).

Next, the above supporting cylinder 5 (on which the water-absorbent resin and the weight 7 had been mounted) was mounted on the center of the filter paper 2. Then, the artificial urine got sucked over a period of 60 minutes since the supporting cylinder 5 had been mounted on the filter paper 2. After 60 minutes, the weight of the supporting cylinder 5 including the water-absorbent resin (which had sucked the artificial urine) and the weight 7 was measured (as weight W2). Then, how large the suction power (g/g) under a load was after 60 minutes from the beginning of the absorption was calculated from these weights W1 and W2 in accordance with the following equation:

$$\text{suction power (g/g) under load}=(\text{weight }W2\text{ (g)}-\text{weight }W1\text{ (g)})/1.0\text{ (g)}.$$

(2) Initial Suction Power Under Load

In the measurement of the suction power under a load as determined in the above way (1), the same operation was carried out except that the operation of sucking the artificial urine over a period of 60 minutes was changed to that over a period of 3 minutes. Specifically, the artificial urine got sucked over a period of 3 minutes, and the weight of the supporting cylinder 5 including the water-absorbent resin (which had sucked the artificial urine) and the weight 7 was measured (as weight W3) after 3 minutes. Then, how large the initial suction power (g/g) under a load was after 3 minutes from the beginning of the absorption was calculated from the following equation:

$$\text{initial suction power (g/g) under load}=(\text{weight }W3\text{ (g)}-\text{weight }W1\text{ (g)})/10.0\text{ (g)}.$$

(3) Suction Index Under Load

The suction index (g/g) under a load was calculated from the suction power under a load and the initial suction power under a load as calculated in the above ways (1) and (2) in accordance with the following equation:

$$\text{suction index (g/g) under a load}=\text{initial suction power (g/g) under load}+\text{suction power (g/g) under load}.$$

(c) Absorption Rate

A beaker of 100 ml in capacity (described in GENERAL CATALOGUE A-7000 published by Sougo Rikagaku Glass Seisakusho Co., Ltd.; TOP beaker, CAT. No. 501, according to JIS R-3503; and body diameter×height=55 (mm)×70 (mm)) is beforehand charged with 50 g of physiological salt solution (its composition was shown below) and a white stirring rod (Teflon (trademark); General catalogue 20,000$^{th}$ edition, published by Flon Industry Co., Ltd.; Teflon (trademark) stirring rod SA model; Product Number: SA-40; and full length 40 mm×diameter 8 mm), wherein the physiological salt solution has beforehand been colored blue and its temperature has beforehand been adjusted to 30° C. Then, they are stirred with a magnetic stirrer at a speed of 600 rpm. When 2.0 g of water-absorbent resin (or particulate water-absorbing composition) is added thereto, the gelation of the test liquid is promoted, and the eddy tends toward decrease, and then the test liquid gets into a state of covering the stirring rod. How long time (seconds) was needed from the addition of the sample till the covering of the stirring rod with the test liquid (till the eddy was about to disappear and the rotating stirring rod as initially seen became unseen by the rise of the eddy) was measured and defined as the absorption rate.

The composition of the physiological salt solution as colored blue is shown below:

| | |
|---|---|
| Deionized water | 991 parts by weight |
| Sodium chloride | 9 parts by weight |
| Food additive, namely, Food blue #1 | 0.02 part by weight |

(Food additive, namely, Food blue #1: disodium benzylethyl-[4'-(4"-(benzylethylamino)-diphenylmethylene)-2',5-cyclohexadienyliden]-ammonium-2''',3,3'''-trisulfonate; brilliant blue-FCF; CI No. 42090; and CI Food blue 2)

(d) Color-Difference

With an SZ-Σ 80 model COLOR MEASURING SYSTEM (produced by Nippon Denshoku Kogyo Co., Ltd.) being used, the color of the water-absorbent resin (or the particulate water-absorbing composition) was measured after XYZ values were corrected on the basis of a standard white board. Then, L, a, b values were determined and defined as the color-difference.

(e) Weight-Average Particle Diameter of Water-Absorbent Resin (and Particulate Water-Absorbing Composition)

Ten grams of water-absorbent resin (and particulate water-absorbing composition) was classified by shaking it with a sieve shaker (IIDA SIEVE SHAKER ES-65 model produced by IIDA SEISAKUSHO CO., LTD.) including JIS standard sieves having an inner diameter of 75 mm (850 µm, 600 µm, 300 µm, 150 µm, and 106 µm) for 5 minutes. Then, there were measured the weights of the following resultant products as classified into their respective particle diameter ranges: 850-µm-on product, 850 to 600 µm, 600 to 300 µm, 300 to 150 µm, 150 to 106 µm, 106-µm-passed products as derived from the above sieves respectively. In addition, the particle diameter distribution of the above-determined particle diameters was plotted on logarithmic probability paper to determine the weight-average particle diameter (D50).

(f) Particle Size of Plant Powder

Ten grams of plant powder was shaken with a sieve shaker (IIDA SIEVE SHAKER ES-65 model produced by IIDA SEISAKUSHO CO., LTD.) fitly including JIS standard sieves having an inner diameter of 75 mm (850 µm, 600 µm, 500 µm, 300 µm, 150 µm, 106 µm, 75 µm, and 45 µm) for 5 minutes under the conditions such as room temperature of 25° C. and relative humidity of 25%. Thus, the particle size of the plant powder was examined.

(g) Water Content of Plant Powder

An aluminum cup (described in GENERAL CATALOGUE A-7000 published by Sougo Rikagaku Glass Seisakusho Co., Ltd.; Aluminum cup, Form: 107; volume=60 ml; and upper diameter×lower diameter×height=65 (mm)×53 (mm)×23 (mm)) was uniformly charged with 1.0 g of plant powder. The weight W (g) was measured after the plant powder was dried with a dryer (NATURAL OVEN NDO-450 produced by TOKYO RIKAKIKAI CO., LTD.) at 105° C. for 3 hours. Then, the water content (%) of the plant powder was calculated from this weight W in accordance with the following equation:

water content (%)=(1.0 (g)−$W$ (g))×100.

(h) Powder Odor Strength

A polypropylene cup of 120 ml in capacity having a cover (produced by Teraoka; Pack-Ace; opening diameter (mm)× bottom diameter (mm)×height (mm)=58×54×74) was charged with 2.0 g of water-absorbent resin (or particulate water-absorbing composition), and this receptacle was covered and then kept at 25° C. The cover was opened after one hour, and then the odor strength was judged by twenty adult panelists' taking a smell about 3 cm apart from the top of the cup.

Each panelist recorded a score according to the following six-rank judgment standard, and then the average thereof was calculated.

0: (Odorless); 1: (very faint); 2: (faint); 3: (easily felt); 4: (strong); 5: (very strong)

(i) Deodorizing Test (Water-Absorbent Resin or Particulate Water-Absorbing Composition)

An amount of 50 ml was picked from a human urine mixture as a collection from 10 adults and then placed into a polypropylene cup of 120 ml in capacity having a cover (produced by Teraoka; Pack-Ace; opening diameter (mm)× bottom diameter (mm)×height (mm)=58×54×74). Then, a swollen gel was formed by adding 2.0 g of water-absorbent resin (or particulate water-absorbing composition) thereto. The human urine was used within 2 hours after having been excreted. This receptacle was covered, and then the swollen gel was kept at 37° C. The cover was opened after 1 minute (initial stage), 3 hours, and 6 hours from the end of the liquid absorption, and then the deodorizing effect was judged by twenty adult panelists' taking a smell about 3 cm apart from the top of the cup.

Each panelist recorded a score according to the following five-rank judgment standard, and then the average thereof was calculated. Incidentally, what was obtained in the same way as above except to add only the human urine without adding the water-absorbent resin (or particulate water-absorbing composition) was defined as a standard sample, and its odor was judged 5 to evaluate the deodorizing effect.

1: (No odor); 2: (odor which is hardly on one's mind); 3: (odor which is perceivable but allowable); 4: (strong odor); 5: (intense odor)

(j) Gel Stability

In a polypropylene cup of 120 ml in capacity having a cover (produced by Teraoka; Pack-Ace; opening diameter (mm)× bottom diameter (mm)×height (mm)=58×54×74), 1 g of water-absorbent resin (or particulate water-absorbing composition) was swollen with 25 ml of artificial urine including L-ascorbic acid in a concentration of 0.005 weight %. This receptacle was covered and then left alone at 37° C. for 16 hours. Thereafter, the gel stability was estimated by the feel of the gel.

The gel stability was estimated according to the following judgment standard. ◯: (The gel is firm); Δ: (The gel is softened); and X: (The gel is entirely collapsed).

The composition of the artificial urine is mentioned below.

| | |
|---|---|
| Deionized water | 97.1 g |
| Urea | 1.9 g |
| Sodium chloride | 0.8 g |
| Magnesium sulfate | 0.1 g |
| Calcium chloride | 0.1 g |

(k) Offensive-Odor Removal Index (l) Hydrogen Sulfide Removal Ratio

A stoppable Erlenmeyer flask of 200 ml in capacity (described in GENERAL CATALOGUE A-7000 published by Sougo Rikagaku Glass Seisakusho Co., Ltd.; TOP Erlenmeyer flask, CAT. No. 506 according to JIS R-3503; and maximum diameter×height=81 (mm)×131 (mm)) was charged with 50 g of aqueous sodium chloride solution of 0.9 weight % (physiological saline) and 10.0 g of water-absorbent resin (or particulate water-absorbing composition) to uniformly swell it. After this Erlenmeyer flask was stopped up with a silicone rubber stopper, a predetermined amount of standard gas was injected through the silicone rubber stopper using a syringe having a needle, and then the flask was left alone at 25° C. After 3 hours, 1 ml of head-space gas was collected through the silicone rubber stopper using a syringe having a needle, and the gas concentration C2 (ppm) was measured by gas chromatography ((Analytical conditions: Instrument=GC-14A produced by Shimadzu Corporation; Detector=FPD; Column temperature=70° C.; Carrier gas=$N_2$; Carrier flow rate=30 ml/min), (Column as used: Manufactory=Shinwa Kako Co., Ltd.; Liquid phase=1,2,3-tris(2-cyanoethoxy)propane 25%; Carrier=Shimalaite AW-DMCS-ST 80 to 100 mesh; Size of column=Φ3 mm×3 M)). In addition, the same procedure was carried out without using either the aqueous sodium chloride solution of 0.9 weight % or the water-absorbent resin (or particulate water-absorbing composition), and then the resultant gas concentration C1(ppm) was measured. Then, the hydrogen sulfide removal ratio (%) was calculated from these concentrations C1 and C2 in accordance with the following equation:

Removal ratio (%)=(gas concentration $C1$−gas concentration $C2$)/gas concentration $C1$×100

The measurement was carried out three times per one kind of the water-absorbent resin (or particulate water-absorbing composition), and then its average value was calculated.

The concentration of the standard gas as used and the amount thereof as injected are mentioned below.

Concentration: Hydrogen sulfide 6,110 ppm/$N_2$ Balance
Amount as injected: 0.82 ml In addition, the method for preparing a calibration curve in measuring the gas concentration is mentioned below.

Gas having concentrations of 1, 3, 10, and 20 ppm respectively were prepared by using the standard gas (hydrogen sulfide 6,110 ppm/$N_2$ balance), and 1 ml thereof was analyzed by gas chromatography, and then the peak area was measured.

The resultant peak area and the gas concentration (ppm) were regarded as X value and Y value respectively, and these values were plotted on a bi-logarithmic graph to prepare the calibration curve.

(2) Methylmercaptan Removal Ratio

A stoppable Erlenmeyer flask of 200 ml in capacity (described in GENERAL CATALOGUE A-7000 published by Sougo Rikagaku Glass Seisakusho Co., Ltd.; TOP Erlenmeyer flask, CAT. No. 506 according to JIS R-3503; and maximum diameter×height=81 (mm)×131 (mm)) was charged with 50 g of aqueous sodium chloride solution of 0.9 weight % (physiological saline) and 10.0 g of water-absorbent resin (or particulate water-absorbing composition) to uniformly swell it. After this Erlenmeyer flask was stopped up with a silicone rubber stopper, a predetermined amount of standard gas was injected through the silicone rubber stopper using a syringe having a needle, and then the flask was left alone at 25° C. After 3 hours, 1 ml of head-space gas was collected through the silicone rubber stopper using a syringe having a needle, and the gas concentration C4 (ppm) was measured by gas chromatography ((Analytical conditions: Instrument=GC-14A produced by Shimadzu Corporation; Detector=FPD; Column temperature=70° C.; Carrier gas=$N_2$; Carrier flow rate=30 ml/min), (Column as used: Manufactory=Shinwa Kako Co., Ltd.; Liquid phase=1,2,3-tris(2-cyanoethoxy)propane 25%; Carrier=Shimalaite AW-DMCS-ST 80 to 100 mesh; Size of column=Φ3 mm×3 M)). In addition, the same procedure was carried out without using either the aqueous sodium chloride solution of 0.9 weight % or the water-absorbent resin (or particulate water-absorbing composition), and then the resultant gas concentration C3 (ppm) was measured. Then, the methylmercaptan removal ratio (%) was calculated from these concentrations C3 and C4 in accordance with the following equation:

Removal ratio (%)=(gas concentration $C3$−gas concentration $C4$)/gas concentration $C3$×100

The measurement was carried out three times per one kind of the water-absorbent resin (or particulate water-absorbing composition), and then its average value was calculated.

The concentration of the standard gas as used and the amount thereof as injected are mentioned below.

Concentration: Methylmercaptan 5,960 ppm/$N_2$ Balance
Amount as injected: 0.84 ml In addition, the method for preparing a calibration curve in measuring the gas concentration is mentioned below.

Gas having concentrations of 1, 3, 10, and 20 ppm respectively were prepared by using the standard gas (methylmercaptan 5,960 ppm/$N_2$ balance), and 1 ml thereof was analyzed by gas chromatography, and then the peak area was measured.

The resultant peak area and the gas concentration (ppm) were regarded as X value and Y value respectively, and these values were plotted on a bi-logarithmic graph to prepare the calibration curve.

(3) Ammonia Removal Ratio

A smelling bag of 3 L in capacity (produced by Ohmi Odor Air Service Co., Ltd.) was charged with 10.0 g of water-absorbent resin (or particulate water-absorbing composition) and 50 g of mixed liquid (comprising aqueous ammonia solution of 29% and aqueous sodium chloride solution of 0.9 weight % in a weight ratio of 1:49) to uniformly swell the water-absorbent resin (or particulate water-absorbing composition). Three liters of odorless air was injected into this smelling bag, and it was left alone at 25° C. after it was stopped up with a silicone rubber stopper. After 3 hours, the silicone rubber stopper was removed, and the contamination by the air outside was inhibited, and then the atmospheric concentration C6 inside the bag was measured with a gas sampler (GV-100S produced by Gastech Co., Ltd.) and a gastic reactotube (No. 3HM, No. 3M, No. 3L produced by Gastech Co., Ltd.). In addition, the same procedure was carried out without using the water-absorbent resin (or particulate water-absorbing composition), and then the resultant atmospheric concentration C5 was measured. Then, the ammonia removal ratio (%) was calculated from these concentrations C5 and C6 in accordance with the following equation:

Removal ratio (%)=(gas concentration $C5$−gas concentration $C6$)/gas concentration $C5$×100

The measurement was carried out three times per one kind of the water-absorbent resin (or particulate water-absorbing composition), and then its average value was calculated.

(4) Offensive-Odor Removal Index

The offensive-odor removal index was calculated by applying the hydrogen sulfide removal ratio, the methylmercaptan removal ratio, and the ammonia removal ratio, as obtained in the above ways (1), (2) and (3), to the following equation:

Offensive-odor removal index=1.1×hydrogen sulfide removal ratio+2.0×methylmercaptan removal ratio+0.3×ammonia removal ratio.

(1) Evaluation of Absorption Properties of Absorbent Article (Absorption Rate and Substantial Absorption Quantity)

Fifty parts by weight of non-powdery fibrous wood pulp and 50 parts by weight of particulate water-absorbing composition were blended together in a dry manner with a mixer. Next, the resultant blend was pneumatically molded on a wire screen of 400 mesh (mesh opening size=38 μm) with a batch-type pneumatic molding apparatus, thereby forming a web having a size of 120 mm×400 mm. Furthermore, this web was pressed under a pressure of 196.14 kPa for 5 seconds, thus obtaining an absorbent structure having a basis weight of about 0.047 g/cm$^2$.

Subsequently, a back sheet (liquid-impermeable sheet) (comprising liquid-impermeable polypropylene and having what is called a leg gather), the above-mentioned absorbent structure, and a top sheet (liquid-impermeable sheet) (comprising liquid-permeable polypropylene) were stuck on each other in this order with a double-coated tape, thus obtaining an absorbent article (namely, an incontinent pad for adults). The weight of this absorbent article was 44 g.

Next, the absorbent article was spread, and thereon a 20-mesh metal gauze having a size of 140 mm×500 mm was mounted. Furthermore thereon an apparatus for measuring the properties of absorbent article under a load, which had a size of 150 mm×400 mm and a weight of 22,000 g in all and was provided with a cylinder of the diameter of 70 mm and the height of 80 mm in the central portion of the apparatus, was mounted between the right and left leg gathers so that the central portion of the cylinder would conform to the center of the absorbent article. Through the cylindrical portion, 150 g of artificial urine (composition: an aqueous solution having a urea content of 1.9 weight %, an NaCl content of 0.8 weight %, a calcium chloride content of 0.1 weight %, and a magnesium sulfate content of 0.1 weight %), of which the temperature had been adjusted to 37° C., was poured all at once. Thereafter, they were left alone for 1 hour, and further 150 g of the artificial urine was poured thereonto all at once. The time passing until the artificial urine was completely absorbed from the top sheet of the absorbent article was observed from above to measure the absorption rate (seconds).

They were left alone for 1 hour after the artificial urine had been poured thereonto for the second time. Thereafter, the apparatus for measuring the properties of the absorbent article under a load and the 20-mesh metal gauze were removed from the absorbent article, and then thereon a paper towel (produced by Oji Seishi Co., Ltd.; Kitchen Towel Extra Dry; 30-ply as cut into the size of 120 mm×450 mm) was mounted, and then thereto a load of 37 g/cm$^2$ (3.63 kPa) was applied for 1 minute to measure the quantity W1 of the liquid returning to the paper towel. In addition, the artificial urine which was not absorbed by the absorbent article but leaked out along the leg gather in a period of 2 hours after the artificial urine had been poured for the first time (in other words, until the amount of the liquid returning to the paper towel was measured) was absorbed by a paper towel (Kitchen Towel Extra Dry produced by Oji Seishi Co., Ltd.) to measure the quantity W2 of the liquid as leaked out.

Then, the substantial absorption quantity (g) as absorbed by the absorbent article was calculated from these liquid quantities W1 and W2 in accordance with the following equation:

$$\text{Substantial absorption quantity (g)}=300\ (g)-(W1\ (g)+W2\ (g))$$

(m) Evaluation of Absorption Properties of Absorbent Article (Deodorizing Test)

Fifty parts by weight of non-powdery fibrous wood pulp and 50 parts by weight of particulate water-absorbing composition were blended together in a dry manner with a mixer. Next, the resultant blend was pneumatically molded on a wire screen of 400 mesh (mesh opening size=38 μm) with a batch-type pneumatic molding apparatus, thereby forming a web having a size of 120 mm×400 mm. Furthermore, this web was pressed under a pressure of 196.14 kPa for 5 seconds, thus obtaining an absorbent structure having a basis weight of about 0.047 g/cm$^2$.

Subsequently, a back sheet (liquid-impermeable sheet) (comprising liquid-impermeable polypropylene and having what is called a leg gather), the above-mentioned absorbent structure, and a top sheet (liquid-impermeable sheet) (comprising liquid-permeable polypropylene) were stuck on each other in this order with a double-coated tape, and beside, the resultant stuck product was provided with what is called two tape fasteners, thus obtaining an absorbent article (namely, a disposable diaper). The weight of this absorbent article was 46 g.

The above absorbent articles were put on ten babies (aged 1) as monitors overnight and then collected the following day. The absorbent structure portion (what is called core portion), comprising the particulate water-absorbing composition and the non-powdery fibrous wood pulp, was cut into the size of 10×10 cm, and then put into a polypropylene cup of 250 ml in capacity having a cover (produced by Teraoka; Pack-Ace; opening diameter (mm)×bottom diameter (mm)×height (mm)=69×63×97). This receptacle was covered and then the temperature of the absorbent structure portion was kept at 37° C. The cover was opened after one hour, and then the deodorizing effect was judged by twenty adult panelists' taking a smell about 3 cm apart from the top of the cup.

Each panelist recorded a score according to the following five-rank judgment standard, and then the average thereof was calculated.

1: (No odor); 2: (odor which is hardly on one's mind); 3: (odor which is perceivable but allowable); 4: (strong odor); 5: (intense odor)

(n) Evaluation of Absorption Properties of Absorbent Article (Dryness Feeling and Deodorizing Effect)

Fifty parts by weight of non-powdery fibrous wood pulp and 50 parts by weight of particulate water-absorbing composition were blended together in a dry manner with a mixer. Next, the resultant blend was pneumatically molded on a wire screen of 400 mesh (mesh opening size=38 μm) with a batch-type pneumatic molding apparatus, thereby forming a web having a size of 120 mm×400 mm. Furthermore, this web was pressed under a pressure of 196.14 kPa for 5 seconds, thus obtaining an absorbent structure having a basis weight of about 0.047 g/cm$^2$.

Subsequently, a back sheet (liquid-impermeable sheet) (comprising liquid-impermeable polypropylene and having what is called a leg gather), the above-mentioned absorbent structure, and a top sheet (liquid-impermeable sheet) (comprising liquid-permeable polypropylene) were stuck on each other in this order with a double-coated tape, thus obtaining an absorbent article (namely, an incontinent pad for adults). The weight of this absorbent article was 44 g.

The above absorbent articles were put on five grown-up men as monitors, who judged a dryness feeling after urination once.

Each man recorded a score according to the following three-rank judgment standard, and then the average thereof was calculated.

1: (Non-sticky to the touch); 2: (feeling slightly wet); 3: (so damp and sticky to the touch as to be unpleasant)

Besides, the absorbent structure portion (what is called core portion), comprising the particulate water-absorbing composition and the non-powdery fibrous wood pulp, was cut into the size of 10×10 cm, and then put into a polypropylene cup of 250 ml in capacity having a cover (produced by Teraoka; Pack-Ace; opening diameter (mm)×bottom diameter (mm)×height (mm)=69×63×97). This receptacle was covered and then the temperature of the absorbent structure portion was kept at 37° C. The cover was opened after 6 hours, and then the deodorizing effect was judged by twenty adult panelists' taking a smell about 3 cm apart from the top of the cup.

Each panelist recorded a score according to the following five-rank judgment standard, and then the average thereof was calculated.

1: (No odor); 2: (odor which is hardly on one's mind); 3: (odor which is perceivable but allowable); 4: (strong odor); 5: (intense odor)

(o) Volume-Average Particle Diameter of Plant Powder

The volume-average particle diameter was measured with SALD-3000 (produced by Shimadzu Corporation).

The measurement was carried out according to a operation manual as prescribed for the SALD-3000. In addition, the weight of the plant powder as used for the measurement was in the range where the absorbance during the measurement was within the measurement range.

Referential Example 1

A reaction liquid was obtained by dissolving 4.00 g of polyethylene glycol diacrylate (molar-number-average degree of addition polymerization of ethylene oxide: 8) into 5,500 g of aqueous sodium acrylate solution having a neutralization ratio of 75 mol % (monomer concentration: 33 weight %). Next, this reaction liquid was deaerated under a nitrogen gas atmosphere for 30 minutes. Next, the reaction liquid was supplied to a reactor as prepared by lidding a jacketed stainless-steel-made twin-arm kneader of 10 liters in capacity having two sigma type blades, and then the internal air of the system was displaced with nitrogen while the reaction liquid was maintained at 30° C. Subsequently, while the reaction liquid was stirred, 2.46 g of sodium persulfate and 0.10 g of L-ascorbic acid were added thereto, with the result that the reaction started after about 1 minute. Then, the polymerization was carried out at 30 to 80° C., and the resultant hydrogel polymer was got out after 60 minutes from the start of the polymerization. The resultant hydrogel polymer was in the form of finely divided pieces having a diameter of about 5 mm. This finely divided hydrogel polymer was spread on a metal gauze of 50 mesh (mesh opening size=300 μm) and then dried with hot air of 150° C. for 90 minutes. Next, the resultant dry material was pulverized with a vibration mill and then classified with a metal gauze of 20 mesh (mesh opening size=850 μm), thus obtaining an irregularly pulverized water-absorbent resin (a) having a weight-average particle diameter of 295 μm.

A surface-crosslinking agent, comprising 1 part by weight of propylene glycol, 0.05 part by weight of ethylene glycol diglycidyl ether, 3 parts by weight of water, and 1 part by weight of isopropyl alcohol, was blended with 100 parts by weight of the resultant water-absorbent resin (a). The resultant mixture was heat-treated at 210° C. for 50 minutes, thus obtaining a water-absorbent resin (1). This water-absorbent resin (1) exhibited an absorption capacity of 33 (g/g), a suction power of 11 (g/g) under a load, and a suction index of 21 (g/g) under a load. In addition, the weight-average particle diameter of this water-absorbent resin was 295 μm which was not very different from that of the original water-absorbent resin.

Referential Example 2

An irregularly pulverized water-absorbent resin (b) having a weight-average particle diameter of 360 μm was obtained in the same way as of Referential Example 1 except that the monomer concentration of the aqueous sodium acrylate solution having a neutralization ratio of 75 mol % was changed to 38 weight %, and that the crosslinking agent was changed from polyethylene glycol diacrylate to 7.0 g of trimethylolpropane triacrylate, and that the pulverization conditions of the vibration mill were changed.

A surface-crosslinking agent, comprising 1 part by weight of propylene glycol, 0.05 part by weight of ethylene glycol diglycidyl ether, 3 parts by weight of water, and 1 part by weight of isopropyl alcohol, was blended with 100 parts by weight of the resultant water-absorbent resin (b). The resultant mixture was heat-treated at 210° C. for 45 minutes, thus obtaining a water-absorbent resin (2). This water-absorbent resin (2) exhibited an absorption capacity of 27 (g/g), a suction power of 11 (g/g) under a load, a suction index of 20 (g/g) under a load, and an absorption rate of 50 seconds. In addition, the weight-average particle diameter of this water-absorbent resin was 360 μm which was not very different from that of the original water-absorbent resin.

Referential Example 3

The irregularly pulverized water-absorbent resin (b) having a weight-average particle diameter of 360 μm, as obtained in Referential Example 2, was regarded as a water-absorbent resin (3), which exhibited an absorption capacity of 32 (g/g), a suction power of 8 (g/g) under a load, and a suction index of 13 (g/g) under a load.

Referential Example 4

An irregularly pulverized water-absorbent resin (c) having a weight-average particle diameter of 440 μm was obtained in the same way as of Referential Example 2 except that the pulverization conditions of the vibration mill were changed. This water-absorbent resin (c) was regarded as a water-absorbent resin (4), which exhibited an absorption capacity of 32 (g/g), a suction power of 8 (g/g) under a load, and a suction index of 13 (g/g) under a load.

Referential Example 5

The irregularly pulverized water-absorbent resin (a) having a weight-average particle diameter of 295 μm, as obtained in Referential Example 1, was regarded as a water-absorbent resin (5), which exhibited an absorption capacity of 45 (g/g), and a suction index of 9 (g/g) under a load.

Examples 1 to 27

The kinds of the water-absorbent resins and plant powders as used are shown together in Table 1. The properties and the deodorizing effects of particulate water-absorbing compositions (1 to 27) are shown together in Tables 3 and 4. In addition, some evaluations of the absorption properties of absorbent articles (1 to 27) including the particulate water-absorbing compositions (1 to 27) are shown together in Table 7.

Hereinafter, production processes of the water-absorbing compositions (1 to 27) are explained.

Example 1

An amount of 100 parts by weight of the water-absorbent resin (1) as obtained in Referential Example 1 was blended with 0.1 part by weight of pepper (White Pepper Powder produced by Takasago Spice Co., Ltd.; this White Pepper Powder had a water content of 10.3%, and a particle diameter 300 μm-passed product thereof was used, and its volume-average particle diameter was 77 μm) as a plant powder by a dry blend method, thus obtaining a particulate water-absorbing composition (1). The resultant particulate water-absorbing composition (1) had a weight-average particle diameter of 295 μm, in which the ratio of particles having particle diameters of smaller than 106 μm was 6 weight %.

Example 2

A particulate water-absorbing composition (2) was obtained in the same way as of Example 1 except that 0.5 part by weight of the pepper was blended by a dry blend method. The resultant particulate water-absorbing composition (2) had a weight-average particle diameter of 295 μm, in which the ratio of particles having particle diameters of smaller than 106 μm was 6 weight %.

Example 3

An amount of 100 parts by weight of the water-absorbent resin (1) as obtained in Referential Example 1 was blended with 0.5 part by weight of Japanese pepper (Japanese Pepper Powder produced by Takasago Spice Co., Ltd.; this Japanese Pepper Powder had a water content of 9.0%, and a particle diameter 500 μm-passed product thereof was used, and its volume-average particle diameter was 172 μm) as a plant powder by a dry blend method, thus obtaining a particulate water-absorbing composition (3). The resultant particulate water-absorbing composition (3) had a weight-average particle diameter of 295 μm, in which the ratio of particles having particle diameters of smaller than 106 μm was 6 weight %.

Example 4

An amount of 100 parts by weight of the water-absorbent resin (1) as obtained in Referential Example 1 was blended with 0.5 part by weight of ginger (Ginger Powder produced by Takasago Spice Co., Ltd.; this Ginger Powder had a water content of 9.1%, and a particle diameter 300 μm-passed product thereof was used, and its volume-average particle diameter was 64 μm) as a plant powder and further with 1.0 part by weight of ion-exchanged water. Thereafter, 0.3 part by weight of silicon dioxide (Aerosil 200 produced by Nippon Aerosil Co., Ltd.) was added as an inorganic powder, thus obtaining a particulate water-absorbing composition (4). The resultant particulate water-absorbing composition (4) had a weight-average particle diameter of 295 μm, in which the ratio of particles having particle diameters of smaller than 106 μm was 5 weight %.

Example 5

An amount of 100 parts by weight of the water-absorbent resin (2) as obtained in Referential Example 2 was blended with 0.5 part by weight of capsicum (Red Pepper Powder produced by Takasago Spice Co., Ltd.; this Red Pepper Powder had a water content of 6.2%, and a particle diameter 500 μm-passed product thereof was used, and its volume-average particle diameter was 244 μm) as a plant powder by a dry blend method, thus obtaining a particulate water-absorbing composition (5). The resultant particulate water-absorbing composition (5) had a weight-average particle diameter of 360 μm, in which the ratio of particles having particle diameters of smaller than 106 μm was 5 weight %.

Example 6

An amount of 100 parts by weight of the water-absorbent resin (2) as obtained in Referential Example 2 was blended with 0.5 part by weight of parsley (Parsley Powder CP produced by Yasuma Co., Ltd.; this Parsley Powder CP had a water content of 6.7%, and a particle diameter 300 μm-passed product thereof was used, and its volume-average particle diameter was 142 μm) as a plant powder by a dry blend method, thus obtaining a particulate water-absorbing composition (6). The resultant particulate water-absorbing composition (6) had a weight-average particle diameter of 360 μm, in which the ratio of particles having particle diameters of smaller than 106 μm was 5 weight %.

Example 7

A particulate water-absorbing composition (7) was obtained in the same way as of Example 6 except that 1.0 part by weight of the parsley was blended by a dry blend method. The resultant particulate water-absorbing composition (7) had a weight-average particle diameter of 360 μm, in which the ratio of particles having particle diameters of smaller than 106 μm was 5 weight %.

Example 8

An amount of 100 parts by weight of the water-absorbent resin (1) as obtained in Referential Example 1 was blended with 0.5 part by weight of green tea (product obtained by pulverizing "green tea (name of raw material) sold by Nishie Corporation (address: 1652-3, Kakiuchikita-machi, Aboshi-ku, Himeji-shi, Hyogo Prefecture, Japan)" with a hammer mill; this pulverized product of green tea had a water content of 2.0%, and a particle diameter 850 μm-passed product thereof was used, and its volume-average particle diameter was 287 μm) as a plant powder by a dry blend method, thus obtaining a particulate water-absorbing composition (8). The resultant particulate water-absorbing composition (8) had a weight-average particle diameter of 295 μm, in which the ratio of particles having particle diameters of smaller than 106 μm was 6 weight %.

Example 9

An amount of 100 parts by weight of the water-absorbent resin (1) as obtained in Referential Example 1 was blended with 0.3 part by weight of milled green tea (sold by Itohen Co., Ltd. (address: 3-47-10, Hon-machi, Shibuya-ku, Tokyo Prefecture, Japan), trade name: Milled Green Tea 30 g with ease, name of raw material: tea; this Milled Green Tea had a water content of 3.4%, and a particle diameter 300 μm-passed product thereof was used, and its volume-average particle diameter was 77 μm) as a plant powder by a dry blend method, thus obtaining a particulate water-absorbing composition (9). The resultant particulate water-absorbing composition (9) had a weight-average particle diameter of 295 μm, in which the ratio of particles having particle diameters of smaller than 106 μm was 6 weight %.

Example 10

An amount of 100 parts by weight of the water-absorbent resin (1) as obtained in Referential Example 1 was blended with 0.5 part by weight of green tea (product obtained by pulverizing "green tea (name of raw material) sold by Nishie Corporation (address: 1652-3, Kakiuchikita-machi, Aboshi-ku, Himeji-shi, Hyogo Prefecture, Japan)" with a hammer mill; this pulverized product of green tea had a water content of 2.4%, and a particle diameter 106 µm-passed product thereof was used) as a plant powder and further with 2.0 parts by weight of ion-exchanged water, thus obtaining a particulate water-absorbing composition (10). The resultant particulate water-absorbing composition (10) had a weight-average particle diameter of 295 µm, in which the ratio of particles having particle diameters of smaller than 106 µm was 4 weight %.

Example 11

An amount of 100 parts by weight of the water-absorbent resin (1) as obtained in Referential Example 1 was blended with 0.5 part by weight of black tea (product obtained by pulverizing "Lipton YELLOW LABEL (trade name) sold by Nippon Lever Co., Ltd. (address: 2-22-3, Shibuya, Shibuya-ku, Tokyo Prefecture, Japan)" with a hammer mill; this pulverized product of black tea had a water content of 6.8%, and a particle diameter 600 µm-passed product thereof was used, and its volume-average particle diameter was 285 µm) as a plant powder by a dry blend method, thus obtaining a particulate water-absorbing composition (11). The resultant particulate water-absorbing composition (11) had a weight-average particle diameter of 295 µm, in which the ratio of particles having particle diameters of smaller than 106 µm was 6 weight %.

Example 12

An amount of 100 parts by weight of the water-absorbent resin (1) as obtained in Referential Example 1 was blended with 0.2 part by weight of oolong tea (product obtained by pulverizing "Oolong Tea (trade name) produced by Ujien Co., Ltd. (address: 2-22, Mikagenaka-machi 1-chome, Higashinada-ku, Kobe-shi, Hyogo Prefecture, Japan)" with a hammer mill; this pulverized product of oolong tea had a water content of 4.8%, and a particle diameter 850 µm-passed product thereof was used, and its volume-average particle diameter was 290 µm) as a plant powder by a dry blend method, thus obtaining a particulate water-absorbing composition (12). The resultant particulate water-absorbing composition (12) had a weight-average particle diameter of 295 µm, in which the ratio of particles having particle diameters of smaller than 106 µm was 6 weight %.

Example 13

An amount of 100 parts by weight of the water-absorbent resin (2) as obtained in Referential Example 2 was blended with 0.5 part by weight of Pu-erh tea (product obtained by pulverizing "Pu-erh Tea (trade name) sold by Ujinotsuyu Seicha Co., Ltd. (address: 50, Kamikomahigashitsukurimi-chi, Yamashiro-cho, Soraku-gun, Kyoto Prefecture, Japan)" with a hammer mill; this pulverized product of Pu-erh tea had a water content of 7.8%, and a particle diameter 600 µm-passed product thereof was used, and its volume-average particle diameter was 256 µm) as a plant powder by a dry blend method, thus obtaining a particulate water-absorbing composition (13). The resultant particulate water-absorbing composition (13) had a weight-average particle diameter of 360 µm, in which the ratio of particles having particle diameters of smaller than 106 µm was 5 weight %.

Example 14

An amount of 100 parts by weight of the water-absorbent resin (2) as obtained in Referential Example 2 was blended with 0.5 part by weight of a dried product of the residue of extraction from green tea (product obtained by adding 10 g of "green tea (name of raw material) sold by Nishie Corporation (address: 1652-3, Kakiuchikita-machi, Aboshi-ku, Himeji-shi, Hyogo Prefecture, Japan)" into 500 g of ion-exchanged water of about 95° C. to blend them together, and then filtrating the resultant mixture after 5 minutes, and then vacuum-drying the filtered-off residue (namely, the residue of extraction from green tea) at 60° C., and then pulverizing the dried product with a hammer mill; this pulverized dried product of the residue of extraction from green tea had a water content of 6.3%, and a particle diameter 850 µm-passed product thereof was used, and its volume-average particle diameter was 346 µm) as a plant powder by a dry blend method, thus obtaining a particulate water-absorbing composition (14). The resultant particulate water-absorbing composition (14) had a weight-average particle diameter of 360 µm, in which the ratio of particles having particle diameters of smaller than 106 µm was 5 weight %.

Example 15

An amount of 100 parts by weight of the water-absorbent resin (2) as obtained in Referential Example 2 was blended with 1.0 part by weight of a dried product of the residue of extraction from black tea (product obtained by adding 10 g of "Lipton YELLOW LABEL (trade name) sold by Nippon Lever Co., Ltd. (address: 2-22-3, Shibuya, Shibuya-ku, Tokyo Prefecture, Japan)" into 500 g of ion-exchanged water of about 95° C. to blend them together, and then filtrating the resultant mixture after 5 minutes, and then vacuum-drying the filtered-off residue (namely, the residue of extraction from black tea) at 60° C., and then pulverizing the dried product with a hammer mill; this pulverized dried product of the residue of extraction from black tea had a water content of 7.9%, and a particle diameter 850 µm-passed product thereof was used, and its volume-average particle diameter was 352 µm) as a plant powder and further with 1.0 part by weight of ion-exchanged water and thereafter with 0.3 part by weight of silicon dioxide (Aerosil 200 produced by Nippon Aerosil Co., Ltd.) as an inorganic powder, thus obtaining a particulate water-absorbing composition (15). The resultant particulate water-absorbing composition (15) had a weight-average particle diameter of 360 µm, in which the ratio of particles having particle diameters of smaller than 106 µm was 4 weight %.

Example 16

An amount of 100 parts by weight of the water-absorbent resin (2) as obtained in Referential Example 2 was blended with 0.5 part by weight of a dried product of the residue of extraction from oolong tea (product obtained by adding 10 g of "Oolong Tea (trade name) produced by Ujien Co., Ltd. (address: 2-22, Mikagenaka-machi 1-chome, Higashinada-ku, Kobe-shi, Hyogo Prefecture, Japan)" into 500 g of ion-exchanged water of about 95° C. to blend them together, and then filtrating the resultant mixture after 5 minutes, and then vacuum-drying the filtered-off residue (namely, the residue of extraction from oolong tea) at 60° C., and then pulverizing the dried product with a hammer mill; this pulverized dried product of the residue of extraction from oolong tea had a water content of 6.5%, and a particle diameter 600 μm-passed product thereof was used, and its volume-average particle diameter was 297 μm) as a plant powder by a dry blend method, thus obtaining a particulate water-absorbing composition (16). The resultant particulate water-absorbing composition (16) had a weight-average particle diameter of 360 μm, in which the ratio of particles having particle diameters of smaller than 106 μm was 5 weight %.

Example 17

An amount of 100 parts by weight of the water-absorbent resin (1) as obtained in Referential Example 1 was blended with 1.0 part by weight of citron (product obtained by pulverizing "Kizami Yuzu (trade name) sold by S&B Foods Co., Ltd. (address: 18-6, Nipponbashi Kabuto-cho, Chuo-ku, Tokyo Prefecture, Japan)" with a hammer mill; this pulverized product of citron had a water content of 8.5%, and a particle diameter 850 μm-passed product thereof was used) as a plant powder and further with 1.0 part by weight of ion-exchanged water, thus obtaining a particulate water-absorbing composition (17). The resultant particulate water-absorbing composition (17) had a weight-average particle diameter of 295 μm, in which the ratio of particles having particle diameters of smaller than 106 μm was 5 weight %.

Example 18

An amount of 100 parts by weight of the water-absorbent resin (1) as obtained in Referential Example 1 was blended with 0.5 part by weight of lime peel (product obtained by peeling a commonly commercially available lime, and then pulverizing the resultant peel with a mixer, and then vacuum-drying the pulverized peel at 60° C., and then further pulverizing the dried product with a hammer mill; this pulverized dried product of lime peel had a water content of 5.6%, and a particle diameter 850 μm-passed product thereof was used) as a plant powder by a dry blend method and further with 2.0 parts by weight of ion-exchanged water, thus obtaining a particulate water-absorbing composition (18). The resultant particulate water-absorbing composition (18) had a weight-average particle diameter of 295 μm, in which the ratio of particles having particle diameters of smaller than 106 μm was 4 weight %.

Example 19

An amount of 100 parts by weight of the water-absorbent resin (1) as obtained in Referential Example 1 was blended with 1.0 part by weight of mandarin orange peel (product obtained by peeling a commonly commercially available mandarin orange (from Arita, Japan), and then pulverizing the resultant peel with a mixer, and then vacuum-drying the pulverized peel at 60° C., and then further pulverizing the dried product with a hammer mill; this pulverized dried product of mandarin orange peel had a water content of 4.5%, and a particle diameter 850 μm-passed product thereof was used) as a plant powder and further with 2.0 parts by weight of ion-exchanged water and thereafter with 0.3 part by weight of silicon dioxide (Aerosil 200 produced by Nippon Aerosil Co., Ltd.) as an inorganic powder, thus obtaining a particulate water-absorbing composition (19). The resultant particulate water-absorbing composition (19) had a weight-average particle diameter of 295 μm, in which the ratio of particles having particle diameters of smaller than 106 μm was 4 weight %.

Example 20

An amount of 100 parts by weight of the water-absorbent resin (1) as obtained in Referential Example 1 was blended with 1.0 part by weight of sea tangle (product obtained by cutting "Hidaka Kizami Wakakombu (product name) produced by Maruzen Naya Shoten (address: 28-1, Shinkawa-cho, Hakodate-shi, Hokkaido Prefecture, Japan)" into as small pieces as possible with scissors, and then pulverizing the resultant pieces with a hammer mill; this pulverized product of sea tangle had a water content of 9.9%, and a particle diameter 850 μm-passed product thereof was used) as a plant powder and further with 1.0 part by weight of ion-exchanged water and thereafter with 0.3 part by weight of silicon dioxide (Aerosil 200 produced by Nippon Aerosil Co., Ltd.) as an inorganic powder, thus obtaining a particulate water-absorbing composition (20). The resultant particulate water-absorbing composition (20) had a weight-average particle diameter of 295 μm, in which the ratio of particles having particle diameters of smaller than 106 μm was 5 weight %.

Example 21

An amount of 100 parts by weight of the water-absorbent resin (1) as obtained in Referential Example 1 was blended with 1.0 part by weight of bamboo cuticle (product obtained by pulverizing "Bamboo Cuticle Powder (trade name) produced by Ban Co., Ltd. (address: 1-98, Tsudakaigan-cho, Tokushima-shi, Tokushima Prefecture, Japan)" with a hammer mill; this pulverized product of Bamboo Cuticle Powder had a water content of 7.0%, and a particle diameter 300 μm-passed product thereof was used) as a plant powder and further with 1.0 part by weight of ion-exchanged water, thus obtaining a particulate water-absorbing composition (21). The resultant particulate water-absorbing composition (21) had a weight-average particle diameter of 295 μm, in which the ratio of particles having particle diameters of smaller than 106 μm was 5 weight %.

Example 22

An amount of 100 parts by weight of the water-absorbent resin (1) as obtained in Referential Example 1 was blended with 1.0 part by weight of residue of extraction from coffee (product obtained by adding 50 g of "Maxim ORIGINAL/original (product name: Regular Coffee) sold by Ajinomoto Co., Ltd. (address: 1-15-1, Kyobashi, Chuo-ku, Tokyo Prefecture, Japan)" into 500 g of ion-exchanged water of about 80° C. to stir them together for 1 hour, and then filtrating the resultant mixture, and then vacuum-drying the filtered-off residue (namely, the residue of extraction from coffee) at 60° C., and then pulverizing the dried product with a hammer mill; this pulverized dried product of the residue of extraction from coffee had a water content of 4.1%, and a particle diameter 850 μm-passed product thereof was used) as a plant powder and further with 1.0 part by weight of ion-exchanged water, thus obtaining a particulate water-absorbing composition (22). The resultant particulate water-absorbing composition (22) had a weight-average particle diameter of 295 μm, in which the ratio of particles having particle diameters of smaller than 106 μm was 5 weight %.

Example 23

An amount of 100 parts by weight of the water-absorbent resin (1) as obtained in Referential Example 1 was blended with 0.5 part by weight of strained grape lees (product obtained by pulverizing commonly commercially available fruit of Delaware trees with a mixer, and then filtrating the pulverized product, and then vacuum-drying the filtered-off residue (namely, the strained grape lees) at 60° C., and then further pulverizing the dried product with a hammer mill; this pulverized dried product of the strained grape lees had a water content of 7.1%, and a particle diameter 500 μm-passed product thereof was used) as a plant powder and further with 1.0 part by weight of ion-exchanged water, thus obtaining a particulate water-absorbing composition (23). The resultant particulate water-absorbing composition (23) had a weight-average particle diameter of 295 μm, in which the ratio of particles having particle diameters of smaller than 106 μm was 5 weight %.

Example 24

An amount of 100 parts by weight of the water-absorbent resin (1) as obtained in Referential Example 1 was blended with 1.0 part by weight of persimmon (product obtained by removing leaves and seeds from commonly commercially available persimmon fruits (hira (in Japanese) persimmon from Wakayama Prefecture, Japan), and then pulverizing the resultant residue with a mixer, and then vacuum-drying the pulverized product at 60° C., and then cutting the dried product into as small pieces as possible with scissors, and then pulverizing the resultant pieces with a hammer mill; this pulverized dried product of persimmon had a water content of 6.4%, and a particle diameter 850 μm-passed product thereof was used) as a plant powder and further with 1.0 part by weight of ion-exchanged water, thus obtaining a particulate water-absorbing composition (24). The resultant particulate water-absorbing composition (24) had a weight-average particle diameter of 295 μm, in which the ratio of particles having particle diameters of smaller than 106 μm was 5 weight %.

Example 25

An amount of 100 parts by weight of the water-absorbent resin (2) as obtained in Referential Example 2 was blended with 1.0 part by weight of mugwort (product obtained by pulverizing leaves of mugwort with a mixer, and then vacuum-drying the pulverized product at 60° C., and then further pulverizing the dried product with a hammer mill; this mugwort powder had a water content of 7.3%, and a particle diameter 300 μm-passed product thereof was used) as a plant powder and further with 1.0 part by weight of ion-exchanged water, thus obtaining a particulate water-absorbing composition (25). The resultant particulate water-absorbing composition (25) had a weight-average particle diameter of 360 μm, in which the ratio of particles having particle diameters of smaller than 106 μm was 4 weight %.

Example 26

An amount of 100 parts by weight of the water-absorbent resin (2) as obtained in Referential Example 2 was blended with 1.0 part by weight of bamboo (product obtained by pulverizing "Bamboo Powder (trade name) produced by Ban Co., Ltd. (address: 1-98, Tsudakaigan-cho, Tokushima-shi, Tokushima Prefecture, Japan)" with a hammer mill; this pulverized product of Bamboo Powder had a water content of 7.9%, and a particle diameter 500 μm-passed product thereof was used) as a plant powder and further with 1.0 part by weight of ion-exchanged water, thus obtaining a particulate water-absorbing composition (26). The resultant particulate water-absorbing composition (26) had a weight-average particle diameter of 360 μm, in which the ratio of particles having particle diameters of smaller than 106 μm was 4 weight %.

Example 27

An amount of 100 parts by weight of the water-absorbent resin (2) as obtained in Referential Example 2 was blended with 1.0 part by weight of wakame (in Japanese) seaweed (product obtained by cutting "Cut Wakame (product name: Dry Wakame) sold by Nagao Foods Co., Ltd.(address: 295, Nobesue, Himeji-shi, Hyogo Prefecture, Japan)" into as small pieces as possible with scissors, and then pulverizing the resultant pieces with a hammer mill; this pulverized product of wakame (in Japanese) seaweed had a water content of 9.5%, and a particle diameter 850 μm-passed product thereof was used) as a plant powder and further with 1.0 part by weight of ion-exchanged water, thus obtaining a particulate water-absorbing composition (27). The resultant particulate water-absorbing composition (27) had a weight-average particle diameter of 360 μm, in which the ratio of particles having particle diameters of smaller than 106 μm was 4 weight %.

Comparative Examples 1 to 31

The kinds of the water-absorbent resins, plant powders, and additives as used are shown together in Table 2. The properties and the deodorizing effects of comparative particulate water-absorbing compositions (1 to 31) are shown together in Tables 5 and 6. In addition, some evaluations of the absorption properties of comparative absorbent articles (1 to 31) including the comparative particulate water-absorbing compositions (1 to 31) are shown together in Table 7.

Hereinafter, production processes of the comparative water-absorbing compositions (1 to 31) are explained.

Comparative Example 1

The water-absorbent resin (1) as obtained in Referential Example 1 was regarded as a comparative particulate water-absorbing composition (1). The resultant comparative particulate water-absorbing composition (1) had a weight-average particle diameter of 295 μm, in which the ratio of particles having particle diameters of smaller than 106 μm was 6 weight %.

Comparative Example 2

An amount of 100 parts by weight of the water-absorbent resin (1) as obtained in Referential Example 1 was blended with 0.5 part by weight of commercially available deodorant comprising a green tea extract (Flavonoid-B produced by Daiichi Kasei Sangyo Co., Ltd.) to obtain a comparative particulate water-absorbing composition (2). The resultant comparative particulate water-absorbing composition (2) had a weight-average particle diameter of 295 μm, in which the ratio of particles having particle diameters of smaller than 106 μm was 6 weight %.

Comparative Example 3

An amount of 100 parts by weight of the water-absorbent resin (1) as obtained in Referential Example 1 was blended with 10 parts by weight of commercially available deodorant comprising a green tea extract (Flavonoid-B produced by Daiichi Kasei Sangyo Co., Ltd.) to obtain a comparative particulate water-absorbing composition (3). The resultant comparative particulate water-absorbing composition (3) had a weight-average particle diameter of 295 μm, in which the ratio of particles having particle diameters of smaller than 106 μm was 3 weight %.

Comparative Example 4

An amount of 100 parts by weight of the water-absorbent resin (3) as obtained in Referential Example 3 was blended with 0.5 part by weight of pepper (White Pepper Powder produced by Takasago Spice Co., Ltd.; this White Pepper Powder had a water content of 10.3%, and a particle diameter 300 μm-passed product thereof was used, and its volume-average particle diameter was 77 μm) as a plant powder by a dry blend method, thus obtaining a comparative particulate water-absorbing composition (4). The resultant comparative particulate water-absorbing composition (4) had a weight-average particle diameter of 360 μm, in which the ratio of particles having particle diameters of smaller than 106 μm was 5 weight %.

Comparative Example 5

An amount of 100 parts by weight of the water-absorbent resin (4) as obtained in Referential Example 4 was blended with 0.5 part by weight of parsley (Parsley Powder CP produced by Yasuma Co., Ltd.; this Parsley Powder CP had a water content of 6.7%, and a particle diameter 300 μm-passed product thereof was used, and its volume-average particle diameter was 142 μm) as a plant powder by a dry blend method, thus obtaining a comparative particulate water-absorbing composition (5). The resultant comparative particulate water-absorbing composition (5) had a weight-average particle diameter of 440 μm, in which the ratio of particles having particle diameters of smaller than 106 μm was 3 weight %.

Comparative Example 6

An amount of 100 parts by weight of the water-absorbent resin (5) as obtained in Referential Example 5 was blended with 0.5 part by weight of pepper (White Pepper Powder produced by Takasago Spice Co., Ltd.; this White Pepper Powder had a water content of 10.3%, and a particle diameter 300 μm-passed product thereof was used) as a plant powder by a dry blend method, thus obtaining a comparative particulate water-absorbing composition (6). The resultant comparative particulate water-absorbing composition (6) had a weight-average particle diameter of 295 μm, in which the ratio of particles having particle diameters of smaller than 106 μm was 6 weight %.

Comparative Example 7

An amount of 100 parts by weight of the water-absorbent resin (5) as obtained in Referential Example 5 was blended with 0.5 part by weight of parsley (Parsley Powder CP produced by Yasuma Co., Ltd.; this Parsley Powder CP had a water content of 6.7%, and a particle diameter 300 μm-passed product thereof was used) as a plant powder by a dry blend method, thus obtaining a comparative particulate water-absorbing composition (7). The resultant comparative particulate water-absorbing composition (7) had a weight-average particle diameter of 295 μm, in which the ratio of particles having particle diameters of smaller than 106 μm was 6 weight %.

Comparative Example 8

An amount of 100 parts by weight of the water-absorbent resin (3) as obtained in Referential Example 3 was blended with 0.5 part by weight of green tea (product obtained by pulverizing "green tea (name of raw material) sold by Nishie Corporation (address: 1652-3, Kakiuchikita-machi, Aboshi-ku, Himeji-shi, Hyogo Prefecture, Japan)" with a hammer mill; this pulverized product of green tea had a water content of 2.0%, and a particle diameter 850 μm-passed product thereof was used, and its volume-average particle diameter was 287 μm) as a plant powder by a dry blend method, thus obtaining a comparative particulate water-absorbing composition (8). The resultant comparative particulate water-absorbing composition (8) had a weight-average particle diameter of 360 μm, in which the ratio of particles having particle diameters of smaller than 106 μm was 5 weight %.

Comparative Example 9

An amount of 100 parts by weight of the water-absorbent resin (4) as obtained in Referential Example 4 was blended with 0.5 part by weight of a dried product of the residue of extraction from green tea (product obtained by adding 10 g of "green tea (name of raw material) sold by Nishie Corporation (address: 1652-3, Kakiuchikita-machi, Aboshi-ku, Himeji-shi, Hyogo Prefecture, Japan)" into 500 g of ion-exchanged water of about 95° C. to blend them together, and then filtrating the resultant mixture after 5 minutes, and then vacuum-drying the filtered-off residue (namely, the residue of extraction from green tea) at 60° C., and then pulverizing the dried product with a hammer mill; this pulverized dried product of the residue of extraction from green tea had a water content of 6.3%, and a particle diameter 850 μm-passed product thereof was used, and its volume-average particle diameter was 346 μm) as a plant powder by a dry blend method, thus obtaining a comparative particulate water-absorbing composition (9). The resultant comparative particulate water-absorbing composition (9) had a weight-average particle diameter of 440 μm, in which the ratio of particles having particle diameters of smaller than 106 μm was 3 weight %.

Comparative Example 10

An amount of 100 parts by weight of the water-absorbent resin (5) as obtained in Referential Example 5 was blended with 50 parts by weight of green tea (green tea (name of raw material) sold by Nishie Corporation (address: 1652-3, Kakiuchikita-machi, Aboshi-ku, Himeji-shi, Hyogo Prefecture, Japan); a particle diameter 600 μm-passed product thereof was used) as a plant powder by a dry blend method, thus obtaining a comparative particulate water-absorbing composition (10). The resultant comparative particulate water-absorbing composition (10) had a weight-average particle diameter of 295 μm, in which the ratio of particles having particle diameters of smaller than 106 μm was 8 weight %.

Comparative Example 11

An amount of 100 parts by weight of the water-absorbent resin (5) as obtained in Referential Example 5 was blended with 0.5 part by weight of mandarin orange peel (product obtained by peeling a commonly commercially available mandarin orange (from Arita, Japan), and then pulverizing the resultant peel with a mixer, and then vacuum-drying the pulverized peel at 60° C., and then further pulverizing the dried product with a hammer mill; this pulverized dried product of mandarin orange peel had a water content of 4.5%, and a particle diameter 850 μm-passed product thereof was used) as a plant powder and further with 1.0 part by weight of ion-exchanged water, thus obtaining a comparative particulate water-absorbing composition (11). The resultant comparative particulate water-absorbing composition (11) had a weight-average particle diameter of 295 μm, in which the ratio of particles having particle diameters of smaller than 106 μm was 5 weight %.

Comparative Example 12

An amount of 100 parts by weight of the water-absorbent resin (5) as obtained in Referential Example 5 was blended with 0.5 part by weight of strained grape lees (product obtained by pulverizing commonly commercially available fruit of Delaware trees with a mixer, and then filtrating the pulverized product, and then vacuum-drying the filtered-off residue (namely, the strained grape lees) at 60° C., and then further pulverizing the dried product with a hammer mill; this pulverized dried product of the strained grape lees had a water content of 7.1%, and a particle diameter 500 μm-passed product thereof was used) as a plant powder and further with 1.0 part by weight of ion-exchanged water, thus obtaining a comparative particulate water-absorbing composition (12). The resultant comparative particulate water-absorbing composition (12) had a weight-average particle diameter of 295 μm, in which the ratio of particles having particle diameters of smaller than 106 μm was 4 weight %.

Comparative Example 13

An amount of 100 parts by weight of the water-absorbent resin (5) as obtained in Referential Example 5 was blended with 1.0 part by weight of persimmon (product obtained by removing leaves and seeds from commonly commercially available persimmon fruits (hira (in Japanese) persimmon from Wakayama Prefecture, Japan), and then pulverizing the resultant residue with a mixer, and then vacuum-drying the pulverized product at 60° C., and then cutting the dried product into as small pieces as possible with scissors, and then pulverizing the resultant pieces with a hammer mill; this pulverized dried product of persimmon had a water content of 6.4%, and a particle diameter 850 μm-passed product thereof was used) as a plant powder and further with 1.0 part by weight of ion-exchanged water, thus obtaining a comparative particulate water-absorbing composition (13). The resultant comparative particulate water-absorbing composition (13) had a weight-average particle diameter of 295 μm, in which the ratio of particles having particle diameters of smaller than 106 μm was 5 weight %.

Comparative Example 14

An amount of 100 parts by weight of the water-absorbent resin (1) as obtained in Referential Example 1 was blended with 1.5 parts by weight of cellulose powder (KC Flock W-200G produced by Nippon Seishi Co., Ltd.) by a dry blend method, thus obtaining a comparative particulate water-absorbing composition (14). The resultant comparative particulate water-absorbing composition (14) had a weight-average particle diameter of 295 μm, in which the ratio of particles having particle diameters of smaller than 106 μm was 8 weight %.

Comparative Example 15

An amount of 100 parts by weight of the water-absorbent resin (1) as obtained in Referential Example 1 was blended with 1.5 parts by weight of cellulose powder (KC Flock W-400G produced by Nippon Seishi Co., Ltd.) by a dry blend method, thus obtaining a comparative particulate water-absorbing composition (15). The resultant comparative particulate water-absorbing composition (15) had a weight-average particle diameter of 295 μm, in which the ratio of particles having particle diameters of smaller than 106 μm was 8 weight %.

Comparative Example 16

An amount of 100 parts by weight of the water-absorbent resin (1) as obtained in Referential Example 1 was blended with 20 parts by weight of cellulose powder (KC Flock W-400G produced by Nippon Seishi Co., Ltd.) by a dry blend method, thus obtaining a comparative particulate water-absorbing composition (16). The resultant comparative particulate water-absorbing composition (16) had a weight-average particle diameter of 260 μm, in which the ratio of particles having particle diameters of smaller than 106 μm was 24 weight %.

Comparative Example 17

An amount of 100 parts by weight of the water-absorbent resin (1) as obtained in Referential Example 1 was blended with 1.0 part by weight of activated carbon (Shirasagi C produced by Takeda Chemical Industries, Ltd.) by a dry blend method, thus obtaining a comparative particulate water-absorbing composition (17). The resultant comparative particulate water-absorbing composition (17) had a weight-average particle diameter of 295 μm, in which the ratio of particles having particle diameters of smaller than 106 μm was 7 weight %.

Comparative Example 18

An amount of 100 parts by weight of the water-absorbent resin (1) as obtained in Referential Example 1 was blended with 1.0 part by weight of tannic acid (Hi Tannic Acid produced by Dainippon Seiyaku Co., Ltd.) and 1.0 part by weight of silicate-salt-mineral-based deodorant (Mizukanite HP produced by Mizusawa Kagaku Kogyo Co., Ltd.), thus obtaining a comparative particulate water-absorbing composition (18). The resultant comparative particulate water-absorbing composition (18) had a weight-average particle diameter of 295 μm, in which the ratio of particles having particle diameters of smaller than 106 μm was 8 weight %.

Comparative Example 19

An amount of 100 parts by weight of the water-absorbent resin (1) as obtained in Referential Example 1 was blended with 1.0 part by weight of commercially available deodorant comprising a green tea extract (Flavonoid-B produced by Daiichi Kasei Sangyo Co., Ltd.) and 1.0 part by weight of silicate-salt-mineral-based deodorant (Mizukanite HP produced by Mizusawa Kagaku Kogyo Co., Ltd.), thus obtaining a comparative particulate water-absorbing composition (19). The resultant comparative particulate water-absorbing composition (19) had a weight-average particle diameter of 295 μm, in which the ratio of particles having particle diameters of smaller than 106 μm was 8 weight %.

Comparative Example 20

An amount of 100 parts by weight of the water-absorbent resin (1) as obtained in Referential Example 1 was blended with 1.0 part by weight of tannic acid (Hi Tannic Acid produced by Dainippon Seiyaku Co., Ltd.) and 9.0 parts by weight of silicate-salt-mineral-based deodorant (Mizukanite HP produced by Mizusawa Kagaku Kogyo Co., Ltd.), thus obtaining a comparative particulate water-absorbing composition (20). The resultant comparative particulate water-absorbing composition (20) had a weight-average particle diameter of 290 μm, in which the ratio of particles having particle diameters of smaller than 106 μm was 11 weight %.

Comparative Example 21

An amount of 100 parts by weight of the water-absorbent resin (1) as obtained in Referential Example 1 was blended with 2 parts by weight of coniferous-tree-extract-supported type deodorant (Isohiba 82 produced by Ensuiko Seito Co., Ltd.), thus obtaining a comparative particulate water-absorbing composition (21). The resultant comparative particulate water-absorbing composition (21) had a weight-average particle diameter of 295 μm, in which the ratio of particles having particle diameters of smaller than 106 μm was 8 weight %.

Comparative Example 22

An amount of 100 parts by weight of the water-absorbent resin (1) as obtained in Referential Example 1 was blended with 0.4 part by weight of commercially available Hiba arbor-vitae oil, thus obtaining a comparative particulate water-absorbing composition (22). The resultant comparative particulate water-absorbing composition (22) had a weight-average particle diameter of 295 μm, in which the ratio of particles having particle diameters of smaller than 106 μm was 6 weight %.

Comparative Example 23

An amount of 100 parts by weight of the water-absorbent resin (1) as obtained in Referential Example 1 was blended with 100 parts by weight of coniferous-tree-extract-supported type deodorant (Isohiba 82 produced by Ensuiko Seito Co., Ltd.), thus obtaining a comparative particulate water-absorbing composition (23). The resultant comparative particulate water-absorbing composition (23) had a weight-average particle diameter of 205 μm, in which the ratio of particles having particle diameters of smaller than 106 μm was 45 weight %.

Comparative Example 24

An amount of 100 parts by weight of the water-absorbent resin (1) as obtained in Referential Example 1 was blended with 20 parts by weight of commercially available Hiba arbor-vitae oil, thus obtaining a comparative particulate water-absorbing composition (24).

Comparative Example 25

An amount of 100 parts by weight of the water-absorbent resin (1) as obtained in Referential Example 1 was blended with 0.4 part by weight of commercially available rosemary, thus obtaining a comparative particulate water-absorbing composition (25). The resultant comparative particulate water-absorbing composition (25) had a weight-average particle diameter of 295 μm, in which the ratio of particles having particle diameters of smaller than 106 μm was 6 weight %.

Comparative Example 26

An amount of 100 parts by weight of the water-absorbent resin (1) as obtained in Referential Example 1 was blended with 10 parts by weight of commercially available rosemary, thus obtaining a comparative particulate water-absorbing composition (26). The resultant comparative particulate water-absorbing composition (26) had a weight-average particle diameter of 295 μm, in which the ratio of particles having particle diameters of smaller than 106 μm was 5 weight %.

Comparative Example 27

An amount of 100 parts by weight of konjak (konnyaku) (in Japanese) (devil's tongue) powder, as a water-absorbent resin, was blended with 0.5 part by weight of ginger (Ginger Powder produced by Takasago Spice Co., Ltd.; this Ginger Powder had a water content of 9.1%, and a particle diameter 300 μm-passed product thereof was used) as a plant powder by a dry blend method, thus obtaining a comparative particulate water-absorbing composition (27). The resultant comparative particulate water-absorbing composition (27) had a weight-average particle diameter of 220 μm, in which the ratio of particles having particle diameters of smaller than 106 μm was 4 weight %.

Comparative Example 28

An amount of 100 parts by weight of konjak (konnyaku) (in Japanese) (devil's tongue) powder, as a water-absorbent resin, was blended with 0.5 part by weight of black tea (product obtained by pulverizing "Lipton YELLOW LABEL (trade name) sold by Nippon Lever Co., Ltd. PT (address: 2-22-3, Shibuya, Shibuya-ku, Tokyo Prefecture, Japan)" with a hammer mill; this pulverized product of black tea had a water content of 6.8%, and a particle diameter 600 μm-passed product thereof was used) as a plant powder by a dry blend method, thus obtaining a comparative particulate water-absorbing composition (28). The resultant comparative particulate water-absorbing composition (28) had a weight-average particle diameter of 220 μm, in which the ratio of particles having particle diameters of smaller than 106 μm was 4 weight %.

Comparative Example 29

An amount of 100 parts by weight of Nonionlex NA-150M (produced by Showa Denko Corporation), as a water-absorbent resin, was blended with 0.5 part by weight of ginger (Ginger Powder produced by Takasago Spice Co., Ltd.; this Ginger Powder had a water content of 9.1%, and a particle diameter 300 μm-passed product thereof was used) as a plant powder by a dry blend method, thus obtaining a comparative particulate water-absorbing composition (29). The resultant comparative particulate water-absorbing composition (29) had a weight-average particle diameter of 490 μm, in which the ratio of particles having particle diameters of smaller than 106 μm was 2 weight %.

Comparative Example 30

An amount of 100 parts by weight of Nonionlex NA-150M (produced by Showa Denko Corporation), as a water-absorbent resin, was blended with 0.5 part by weight of black tea (product obtained by pulverizing "Lipton YELLOW LABEL (trade name) sold by Nippon Lever Co., Ltd. PT (address: 2-22-3, Shibuya, Shibuya-ku, Tokyo Prefecture, Japan)" with a hammer mill; this pulverized product of black tea had a water content of 6.8%, and a particle diameter 600 μm-passed product thereof was used) as a plant powder by a dry blend method, thus obtaining a comparative particulate water-absorbing composition (30). The resultant comparative particulate water-absorbing composition (30) had a weight-average particle diameter of 490 μm, in which the ratio of particles having particle diameters of smaller than 106 μm was 2 weight %.

Comparative Example 31

An amount of 100 parts by weight of Nonionlex NA-150M (produced by Showa Denko Corporation), as a water-absorbent resin, was blended with 1.0 part by weight of sea tangle (product obtained by cutting "Hidaka Kizami Wakakombu (product name) produced by Maruzen Naya Shoten (address: 28-1, Shinkawa-cho, Hakodate-shi, Hokkaido Prefecture, Japan)" into as small pieces as possible with scissors, and then pulverizing the resultant pieces with a hammer mill; this pulverized product of sea tangle had a water content of 9.9%, and a particle diameter 850 μm-passed product thereof was used) as a plant powder by a dry blend method, thus obtaining a comparative particulate water-absorbing composition (31). The resultant comparative particulate water-absorbing composition (31) had a weight-average particle diameter of 490 μm, in which the ratio of particles having particle diameters of smaller than 106 μm was 2 weight %.

TABLE 1

| Example | Water-absorbent resin | Kind of plant powder or additive I | II | Water-absorbing composition |
|---|---|---|---|---|
| 1 | Water-absorbent resin (1) | Pepper | — | Water-absorbing composition (1) |
| 2 | Water-absorbent resin (1) | Pepper | — | Water-absorbing composition (2) |
| 3 | Water-absorbent resin (1) | Japanese pepper | — | Water-absorbing composition (3) |
| 4 | Water-absorbent resin (1) | Ginger | — | Water-absorbing composition (4) |
| 5 | Water-absorbent resin (2) | Capsicum | — | Water-absorbing composition (5) |
| 6 | Water-absorbent resin (2) | Parsley | — | Water-absorbing composition (6) |
| 7 | Water-absorbent resin (2) | Parsley | — | Water-absorbing composition (7) |
| 8 | Water-absorbent resin (1) | Green tea | — | Water-absorbing composition (8) |
| 9 | Water-absorbent resin (1) | Milled green tea | — | Water-absorbing composition (9) |
| 10 | Water-absorbent resin (1) | Green tea | — | Water-absorbing composition (10) |
| 11 | Water-absorbent resin (1) | Black tea | — | Water-absorbing composition (11) |
| 12 | Water-absorbent resin (1) | Oolong tea | — | Water-absorbing composition (12) |
| 13 | Water-absorbent resin (2) | Pu-erh tea | — | Water-absorbing composition (13) |
| 14 | Water-absorbent resin (2) | Residue of extraction from green tea | — | Water-absorbing composition (14) |
| 15 | Water-absorbent resin (2) | Residue of extraction from black tea | — | Water-absorbing composition (15) |
| 16 | Water-absorbent resin (2) | Residue of extraction from oolong tea | — | Water-absorbing composition (16) |
| 17 | Water-absorbent resin (1) | Citron | — | Water-absorbing composition (17) |
| 18 | Water-absorbent resin (1) | Lime peel | — | Water-absorbing composition (18) |
| 19 | Water-absorbent resin (1) | Mandarin orange peel | — | Water-absorbing composition (19) |
| 20 | Water-absorbent resin (1) | Sea tangle | — | Water-absorbing composition (20) |
| 21 | Water-absorbent resin (1) | Bamboo cuticle | — | Water-absorbing composition (21) |
| 22 | Water-absorbent resin (1) | Residue of extraction from coffee | — | Water-absorbing composition (22) |
| 23 | Water-absorbent resin (1) | Strained grape lees | — | Water-absorbing composition (23) |
| 24 | Water-absorbent resin (1) | Persimmon | — | Water-absorbing composition (24) |
| 25 | Water-absorbent resin (2) | Mugwort | — | Water-absorbing composition (25) |
| 26 | Water-absorbent resin (2) | Bamboo | — | Water-absorbing composition (26) |
| 27 | Water-absorbent resin (2) | Wakame seaweed | — | Water-absorbing composition (27) |

TABLE 2

| Comparative Example | Water-absorbent resin | Kind of plant powder or additive I | II | Water-absorbing composition |
|---|---|---|---|---|
| 1 | Water-absorbent resin (1) | — | — | Comparative water-absorbing composition (1) |
| 2 | Water-absorbent resin (1) | Green tea extract | — | Comparative water-absorbing composition (2) |
| 3 | Water-absorbent resin (1) | Green tea extract | — | Comparative water-absorbing composition (3) |
| 4 | Water-absorbent resin (3) | Pepper | — | Comparative water-absorbing composition (4) |
| 5 | Water-absorbent resin (4) | Parsley | — | Comparative water-absorbing composition (5) |
| 6 | Water-absorbent resin (5) | Pepper | — | Comparative water-absorbing composition (6) |
| 7 | Water-absorbent resin (5) | Parsley | — | Comparative water-absorbing composition (7) |
| 8 | Water-absorbent resin (3) | Green tea | — | Comparative water-absorbing composition (8) |
| 9 | Water-absorbent resin (4) | Residue of extraction from green tea | — | Comparative water-absorbing composition (9) |
| 10 | Water-absorbent resin (5) | Green tea | — | Comparative water-absorbing composition (10) |

TABLE 2-continued

| Comparative Example | Water-absorbent resin | Kind of plant powder or additive I | II | Water-absorbing composition |
|---|---|---|---|---|
| 11 | Water-absorbent resin (5) | Mandarin orange peel | — | Comparative water-absorbing composition (11) |
| 12 | Water-absorbent resin (5) | Strained grape lees | — | Comparative water-absorbing composition (12) |
| 13 | Water-absorbent resin (5) | Persimmon | — | Comparative water-absorbing composition (13) |
| 14 | Water-absorbent resin (1) | Cellulose powder | — | Comparative water-absorbing composition (14) |
| 15 | Water-absorbent resin (1) | Cellulose powder | — | Comparative water-absorbing composition (15) |
| 16 | Water-absorbent resin (1) | Cellulose powder | — | Comparative water-absorbing composition (16) |
| 17 | Water-absorbent resin (1) | Activated carbon | — | Comparative water-absorbing composition (17) |
| 18 | Water-absorbing resin (1) | Tannic acid | Silicate salt mineral | Comparative water-absorbing composition (18) |
| 19 | Water-absorbent resin (1) | Green tea extract | Silicate salt mineral | Comparative water-absorbing composition (19) |
| 20 | Water-absorbent resin (1) | Tannic acid | Silicate salt mineral | Comparative water-absorbing composition (20) |
| 21 | Water-absorbent resin (1) | Coniferous-tree-extract-supported type deodorant | — | Comparative water-absorbing composition (21) |
| 22 | Water-absorbent resin (1) | Hiba arbor-vitae oil | — | Comparative water-absorbing composition (22) |
| 23 | Water-absorbent resin (1) | Coniferous-tree-extract-supported type deodorant | — | Comparative water-absorbing composition (23) |
| 24 | Water-absorbent resin (1) | Hiba arbor-vitae oil | — | Comparative water-absorbing composition (24) |
| 25 | Water-absorbent resin (1) | Rosemary | — | Comparative water-absorbing composition (25) |
| 26 | Water-absorbent resin (1) | Rosemary | — | Comparative water-absorbing composition (26) |
| 27 | Konjak (konnyaku) powder | Ginger | — | Comparative water-absorbing composition (27) |
| 28 | Konjak (konnyaku) pwder | Black tea | — | Comparative water-absorbing composition (28) |
| 29 | Nonionlex | Ginger | — | Comparative water-absorbing composition (29) |
| 30 | Nonionlex | Black tea | — | Comparative water-absorbing composition (30) |
| 31 | Nonionlex | Sea tangle | — | Comparative water-absorbing composition (31) |

TABLE 3

| Example | Absorption capacity (g/g) | Initial suction power under load (g/g) | Suction power under load (g/g) | Suction index under load (g/g) | Absorption rate (seconds) | Color-difference L | a | b |
|---|---|---|---|---|---|---|---|---|
| 1 | 33 | 10 | 11 | 21 | 37 | 87.32 | −0.51 | 7.35 |
| 2 | 33 | 10 | 11 | 21 | 37 | 86.01 | −0.56 | 7.70 |
| 3 | 33 | 10 | 11 | 21 | 37 | 81.64 | 0.29 | 7.32 |
| 4 | 32 | 9 | 10 | 19 | 29 | 87.70 | −0.42 | 9.21 |
| 5 | 27 | 9 | 11 | 20 | 50 | 80.80 | 3.06 | 10.84 |
| 6 | 27 | 9 | 11 | 20 | 50 | 74.80 | −3.27 | 8.66 |
| 7 | 27 | 9 | 11 | 20 | 50 | 70.56 | −3.92 | 9.60 |
| 8 | 33 | 10 | 11 | 21 | 37 | 84.10 | −0.67 | 5.82 |
| 9 | 33 | 10 | 11 | 21 | 37 | 78.86 | −1.25 | 9.22 |
| 10 | 33 | 10 | 11 | 21 | 37 | 71.88 | −1.83 | 10.01 |
| 11 | 33 | 10 | 11 | 21 | 37 | 72.58 | 0.63 | 5.02 |
| 12 | 33 | 10 | 11 | 21 | 37 | 85.03 | −0.16 | 5.71 |
| 13 | 27 | 9 | 11 | 20 | 50 | 76.42 | 0.33 | 4.26 |
| 14 | 27 | 9 | 11 | 20 | 50 | 85.89 | −0.51 | 5.98 |
| 15 | 26 | 8 | 10 | 18 | 42 | 72.01 | 1.09 | 5.67 |
| 16 | 27 | 9 | 11 | 20 | 50 | 73.22 | 0.51 | 4.92 |
| 17 | 33 | 10 | 11 | 21 | 37 | 87.28 | −0.86 | 9.54 |
| 18 | 33 | 10 | 11 | 21 | 37 | 86.95 | −0.92 | 6.92 |
| 19 | 32 | 9 | 10 | 19 | 29 | 86.02 | −0.38 | 9.69 |
| 20 | 32 | 9 | 10 | 19 | 29 | 83.36 | −0.98 | 6.43 |
| 21 | 33 | 10 | 11 | 21 | 37 | 82.48 | −2.05 | 11.41 |
| 22 | 33 | 10 | 11 | 21 | 37 | 77.20 | 0.96 | 6.97 |

TABLE 3-continued

| Example | Absorption capacity (g/g) | Initial suction power under load (g/g) | Suction power under load (g/g) | Suction index under load (g/g) | Absorption rate (seconds) | Color-difference L | a | b |
|---|---|---|---|---|---|---|---|---|
| 23 | 33 | 10 | 11 | 21 | 37 | 79.08 | 0.68 | 3.55 |
| 24 | 33 | 10 | 11 | 21 | 37 | 86.30 | −0.31 | 7.07 |
| 25 | 27 | 9 | 11 | 20 | 50 | 60.94 | −4.77 | 9.97 |
| 26 | 27 | 9 | 11 | 20 | 50 | 86.19 | −0.18 | 8.96 |
| 27 | 27 | 9 | 11 | 20 | 50 | 74.16 | −2.41 | 5.83 |

TABLE 4

| Example | Powder odor | Deodorizing effect Initial | 3 hours | 6 hours | Offensive-odor removal ratio (%) Hydrogen sulfide | Methylmercaptan | Ammonia | Offensive-odor removal index | Gel stability |
|---|---|---|---|---|---|---|---|---|---|
| 1 | 0.4 | 2.4 | 2.5 | 2.7 | 42.8 | 53.0 | 99.9 | 183 | Δ |
| 2 | 0.6 | 2.1 | 2.3 | 2.4 | 54.1 | 54.9 | 99.9 | 199 | ○ |
| 3 | 0.7 | 1.6 | 1.7 | 1.8 | 61.1 | 89.0 | 99.9 | 275 | ○ |
| 4 | 1.3 | 1.5 | 1.7 | 2.6 | 60.0 | 82.2 | 100.0 | 260 | ○ |
| 5 | 1.8 | 1.6 | 1.6 | 1.7 | 81.7 | 85.6 | 99.9 | 291 | ○ |
| 6 | 1.8 | 1.9 | 2.3 | 3.0 | 77.7 | 95.1 | 99.9 | 306 | ○ |
| 7 | 1.9 | 1.8 | 2.4 | 3.1 | 82.5 | 96.4 | 99.9 | 314 | ○ |
| 8 | 1.5 | 2.2 | 2.4 | 2.8 | 53.5 | 56.1 | 99.9 | 201 | ○ |
| 9 | 1.4 | 1.8 | 2.0 | 2.3 | 65.0 | 72.0 | 99.9 | 245 | ○ |
| 10 | 1.9 | 1.8 | 1.9 | 2.0 | 73.1 | 79.2 | 99.8 | 269 | ○ |
| 11 | 1.2 | 2.2 | 2.2 | 2.2 | 74.1 | 78.1 | 99.9 | 268 | ○ |
| 12 | 0.8 | 2.4 | 2.4 | 2.6 | 58.6 | 66.2 | 99.9 | 227 | ○ |
| 13 | 0.9 | 2.7 | 2.7 | 3.1 | 89.3 | 96.4 | 99.9 | 321 | ○ |
| 14 | 1.0 | 2.4 | 2.7 | 2.9 | 47.2 | 53.8 | 99.9 | 189 | ○ |
| 15 | 1.4 | 2.5 | 2.6 | 2.8 | 67.8 | 72.3 | 99.9 | 249 | ○ |
| 16 | 1.3 | 2.4 | 2.6 | 2.9 | 52.1 | 64.7 | 99.9 | 217 | ○ |
| 17 | 1.6 | 2.0 | 2.3 | 2.5 | 57.8 | 72.2 | 99.9 | 238 | ○ |
| 18 | 1.3 | 2.3 | 2.4 | 2.6 | 49.5 | 70.3 | 99.9 | 225 | ○ |
| 19 | 1.7 | 2.0 | 2.1 | 2.4 | 87.1 | 90.2 | 99.9 | 306 | ○ |
| 20 | 0.7 | 2.4 | 2.4 | 2.9 | 86.9 | 79.4 | 99.9 | 284 | ○ |
| 21 | 0.3 | 2.4 | 2.4 | 2.5 | 51.7 | 78.2 | 99.7 | 243 | ○ |
| 22 | 2.4 | 2.0 | 2.3 | 2.5 | 59.7 | 60.5 | 99.9 | 217 | ○ |
| 23 | 1.1 | 2.5 | 2.6 | 2.8 | 73.1 | 86.2 | 99.9 | 283 | ○ |
| 24 | 1.0 | 2.5 | 2.7 | 2.9 | 78.1 | 86.9 | 99.9 | 290 | ○ |
| 25 | 2.1 | 1.8 | 1.9 | 2.0 | 77.9 | 83.2 | 99.9 | 282 | ○ |
| 26 | 0.8 | 2.3 | 2.3 | 2.3 | 53.1 | 76.2 | 99.9 | 241 | ○ |
| 27 | 1.2 | 2.4 | 2.6 | 2.8 | 76.0 | 77.7 | 99.9 | 269 | ○ |

TABLE 5

| Comparative Example | Absorption capacity (g/g) | Initial suction power under load (g/g) | Suction power under load (g/g) | Suction index under load (g/g) | Absorption rate (seconds) | Color-difference L | a | b |
|---|---|---|---|---|---|---|---|---|
| 1 | 33 | 10 | 11 | 21 | 37 | 89.75 | −0.33 | 7.09 |
| 2 | 33 | 10 | 11 | 21 | 37 | 88.92 | −0.47 | 6.76 |
| 3 | 32 | 10 | 11 | 21 | 33 | 88.30 | −0.51 | 6.54 |
| 4 | 32 | 5 | 8 | 13 | 25 | 85.85 | −0.47 | 7.75 |
| 5 | 32 | 5 | 8 | 13 | 53 | 76.82 | −2.84 | 8.20 |
| 6 | 45 | 3 | 6 | 9 | 21 | 86.23 | −0.55 | 7.52 |
| 7 | 45 | 3 | 6 | 9 | 21 | 78.99 | −2.61 | 8.12 |
| 8 | 32 | 5 | 8 | 13 | 25 | 84.36 | −0.58 | 5.85 |
| 9 | 32 | 5 | 8 | 13 | 53 | 86.02 | −0.57 | 6.24 |
| 10 | 28 | 4 | 6 | 10 | 44 | 39.94 | −4.42 | 10.58 |
| 11 | 45 | 3 | 6 | 9 | 21 | 88.38 | −0.35 | 8.51 |
| 12 | 45 | 3 | 6 | 9 | 21 | 79.59 | 0.72 | 3.65 |
| 13 | 45 | 3 | 6 | 9 | 21 | 86.43 | −0.32 | 6.53 |
| 14 | 34 | 10 | 12 | 22 | 43 | 89.15 | −0.53 | 6.38 |
| 15 | 34 | 10 | 12 | 22 | 43 | 89.37 | −0.43 | 6.17 |
| 16 | 29 | 10 | 13 | 23 | 54 | 93.69 | −0.18 | 5.24 |
| 17 | 33 | 10 | 11 | 21 | 37 | 25.80 | 0.13 | 0.49 |
| 18 | 34 | 10 | 11 | 21 | 37 | 87.06 | 0.18 | 8.79 |
| 19 | 34 | 10 | 11 | 21 | 37 | 89.83 | −0.30 | 5.69 |
| 20 | 30 | 10 | 11 | 21 | 39 | 90.95 | 0.28 | 5.76 |
| 21 | 34 | 10 | 10 | 20 | 38 | 89.24 | −1.10 | 7.92 |

TABLE 5-continued

| Comparative Example | Absorption capacity (g/g) | Initial suction power under load (g/g) | Suction power under load (g/g) | Suction index under load (g/g) | Absorption rate (seconds) | Color-difference L | a | b |
|---|---|---|---|---|---|---|---|---|
| 22 | 36 | 10 | 11 | 21 | 38 | 87.77 | −0.63 | 6.89 |
| 23 | 18 | 2 | 8 | 10 | 196 | 95.14 | −3.71 | 13.45 |
| 24 | 31 | 8 | 9 | 17 | 55 | 75.66 | −2.66 | 10.26 |
| 25 | 35 | 10 | 11 | 21 | 39 | 88.51 | −0.46 | 6.59 |
| 26 | 35 | 10 | 11 | 21 | 39 | 88.63 | −0.41 | 7.22 |
| 27 | 18 | 4 | 5 | 9 | 100 | 74.69 | 0.84 | 15.25 |
| 28 | 18 | 4 | 5 | 9 | 100 | 73.25 | 0.89 | 16.52 |
| 29 | 23 | 2 | 5 | 7 | 65 | 90.80 | −0.72 | 3.87 |
| 30 | 23 | 2 | 5 | 7 | 65 | 90.37 | −0.68 | 4.02 |
| 31 | 23 | 2 | 5 | 7 | 65 | 90.51 | −0.85 | 4.29 |

TABLE 6

| Comparative Example | Powder odor | Deodorizing effect Initial | 3 hours | 6 hours | Offensive-odor removal ratio (%) Hydrogen sulfide | Methylmercaptan | Ammonia | Offensive-odor removal index | Gel stability |
|---|---|---|---|---|---|---|---|---|---|
| 1 | 0.2 | 4.0 | 4.3 | 5.0 | 35.2 | 46.5 | 99.9 | 162 | x |
| 2 | 0.7 | 3.3 | 3.6 | 4.0 | — | — | — | — | x |
| 3 | 1.3 | 3.0 | 3.3 | 3.8 | — | — | — | — | x |
| 4 | 0.6 | 4.1 | 4.1 | 4.2 | 30.4 | 38.6 | 99.4 | 140 | x |
| 5 | 1.7 | 3.9 | 4.0 | 4.2 | 36.8 | 45.3 | 99.5 | 161 | x |
| 6 | 0.4 | 4.0 | 4.0 | 4.3 | 7.1 | 25.9 | 98.6 | 89 | x |
| 7 | 1.8 | 4.0 | 4.0 | 4.2 | 26.6 | 37.7 | 98.8 | 134 | x |
| 8 | 1.6 | 3.2 | 3.3 | 3.8 | 38.4 | 49.7 | 99.1 | 171 | x |
| 9 | 1.2 | 3.4 | 3.5 | 3.9 | 34.6 | 46.4 | 99.3 | 161 | x |
| 10 | 4.1 | 3.2 | 3.3 | 3.6 | — | — | — | — | x |
| 11 | 1.5 | 3.4 | 3.6 | 3.9 | 30.2 | 32.9 | 98.6 | 129 | x |
| 12 | 0.7 | 3.5 | 3.8 | 4.0 | 24.7 | 32.8 | 98.9 | 122 | x |
| 13 | 1.2 | 3.3 | 3.7 | 3.9 | 24.6 | 33.2 | 98.8 | 123 | x |
| 14 | 0.8 | 3.6 | 3.9 | 4.2 | 36.9 | 49.3 | 99.8 | 169 | ○ |
| 15 | 0.9 | 3.3 | 3.5 | 4.0 | 36.7 | 48.7 | 99.8 | 168 | ○ |
| 16 | 1.6 | 3.5 | 3.7 | 4.2 | 39.1 | 52.5 | 99.7 | 178 | ○ |
| 17 | 0.7 | 1.8 | 2.0 | 2.4 | — | — | — | — | ○ |
| 18 | 0.3 | 3.3 | 3.5 | 3.8 | — | — | — | — | ○ |
| 19 | 0.4 | 3.1 | 3.4 | 3.7 | — | — | — | — | ○ |
| 20 | 0.3 | 3.3 | 3.5 | 3.7 | — | — | — | — | ○ |
| 21 | 4.3 | 1.0 | 1.3 | 1.8 | — | — | — | — | Δ |
| 22 | 4.5 | 1.0 | 1.0 | 1.4 | — | — | — | — | Δ |
| 23 | 5.0 | 1.0 | 1.0 | 1.2 | — | — | — | — | x |
| 24 | 5.0 | 1.0 | 1.0 | 1.2 | — | — | — | — | x |
| 25 | 4.7 | 1.8 | 2.0 | 2.3 | — | — | — | — | Δ |
| 26 | 5.0 | 1.0 | 1.0 | 1.3 | — | — | — | — | x |
| 27 | 4.6 | 3.6 | 3.8 | 4.4 | 64.8 | 13.9 | 16.7 | 104 | x |
| 28 | 4.5 | 3.7 | 3.9 | 4.3 | 65.2 | 16.4 | 18.3 | 110 | x |
| 29 | 1.2 | 4.4 | 4.4 | 4.5 | 11.0 | 21.8 | 0.0 | 56 | x |
| 30 | 1.1 | 4.3 | 4.5 | 4.6 | 10.5 | 20.3 | 0.0 | 52 | x |
| 31 | 1.2 | 4.5 | 4.6 | 4.8 | 13.2 | 20.6 | 0.0 | 56 | x |

TABLE 7

| Water-absorbing composition as used | Evaluation of absorption properties of absorbent article | | | | Evaluation of absorption properties of absorbent article | Evaluation of absorption properties of absorbent article | |
|---|---|---|---|---|---|---|---|
| | Absorption rate (seconds) | Amount as leaked out (g) | Amount of returning (g) | Substantial absorption quantity (g) | Deodorizing test | Dryness feeling | Deodorizing effect |
| Water-absorbing composition (3) | 288 | 1 | 22 | 277 | 20 | 12 | 2.4 |
| Water-absorbing composition (6) | 401 | 2 | 50 | 248 | 24 | 14 | 16 |
| Water-absorbing composition (8) | 312 | 3 | 22 | 275 | 24 | 14 | 21 |
| Water-absorbing composition (10) | 296 | 4 | 23 | 273 | 21 | 12 | 19 |
| Water-absorbing composition (11) | 290 | 6 | 22 | 272 | 20 | 12 | 23 |
| Water-absorbing composition (17) | 315 | 4 | 24 | 272 | 20 | 14 | 21 |
| Water-absorbing composition (19) | 338 | 3 | 43 | 254 | 2.0 | 12 | 21 |
| Water-absorbing composition (21) | 295 | 5 | 22 | 273 | 23 | 1.2 | 24 |
| Water-absorbing composition (25) | 427 | 4 | 48 | 248 | 2.1 | 14 | 2.5 |

TABLE 7-continued

| Water-absorbing composition as used | Evaluation of absorption properties of absorbent article | | | | Evaluation of absorption properties of absorbent article | Evaluation of absorption properties of absorbent article | |
|---|---|---|---|---|---|---|---|
| | Absorption rate (seconds) | Amount as leaked out (g) | Amount of returning (g) | Substantial absorption quantity (g) | Deodorizing test | Dryness feeling | Deodorizing effect |
| Water-absorbing composition (26) | 422 | 3 | 48 | 249 | 21 | 14 | 16 |
| Comparative water-absorbing composition (1) | 293 | 1 | 24 | 275 | 40 | 12 | 43 |
| Comparative water-absorbing composition (6) | 2,102 | 30 | 40 | 230 | 36 | 26 | 39 |
| Comparative water-absorbing composition (8) | 1,447 | 16 | 48 | 236 | 36 | 28 | 37 |
| Comparative water-absorbing composition (14) | 305 | 7 | 22 | 271 | 40 | 14 | 45 |
| Comparative water-absorbing composition (18) | 810 | 5 | 50 | 245 | 36 | 16 | 42 |
| Comparative water-absorbing composition (28) | Not less than 3,600 | 97 | 55 | 148 | 44 | 3.0 | 44 |
| Comparative water-absorbing composition (30) | Not less than 3,600 | 67 | 57 | 176 | 42 | 30 | 43 |

INDUSTRIAL APPLICATION

The particulate water-absorbing composition according to the present invention is a new particulate water-absorbing composition which can provide the deodorizing function to absorbent articles and exhibits excellent deodorizability and excellent absorption properties for a long time. Although not clear, the cause is considered to be probably that since the water-absorbent resin is limited to such as exhibits the specific absorption capacity, suction power under a load, and absorption rate and since such a water-absorbent resin is provided with the plant powder, the optimum balance between the action of effective components of the plant powder and the liquid absorption quantity upon contact with urine has been achieved.

In addition, since the above absorbent article according to the present invention includes the particulate water-absorbing composition according to the present invention and can therefore be provided with excellent deodorizability of this composition, this absorbent article is favorably usable particularly for sanitary materials such as disposable diapers, sanitary napkins, incontinent pads for adults, and diapers for adults, and can be what is able to retain an excellent wearing feeling for a long time because of further being provided with the gel stability.

The invention claimed is:

1. A particulate water-absorbing composition, which comprises a Tracheophyta plant powder and a water-absorbent resin, wherein the water-absorbent resin is a water-swellable and water-insoluble crosslinked poly(acrylic acid (salt)) polymer of 30 to 100 mol % in neutralization ratio having a surface portion and/or its vicinity treated by crosslinking with a crosslinking agent and is contained in a proportion of not less than 70 weight % in the particulate water-absorbing composition, and wherein the particulate water-absorbing composition is in the range of 100 to 600 μm in weight-average particle diameter and not more than 10 weight % in proportion of particles having particle diameters of smaller than 106 μm, and wherein the Tracheophyta plant powder passes through a mesh having a mesh opening size of 850 μm, and wherein the content of the Tracheophyta plant powder is in the range of 0.001 to 20 weight parts per 100 weight parts of the solid content of the water-absorbent resin, and wherein said content of the Tracheophyta plant powder is an amount effective for the particulate water-absorbing composition to exhibit an offensive-odor removal index of not less than 180 wherein the offensive-odor removal index is represented by the following equation:

offensive-odor removal index=1.1×hydrogen sulfide removal ratio+2.0×methylmercaptan removal ratio+0.3×ammonia removal ratio.

2. A particulate water-absorbing composition according to claim 1, wherein the Tracheophyta plant is at least one kind of Tracheophyta plant selected from the group consisting of Gramineae, maple family, Ebenaceae, Betulaceae, Compositae, Lamiaceae, cryptomeria family, Umbelliferae, Rosaceae, Vitaceae, Japanese cypress family, pine family, Fagaceae, Brassicaceae, Leguminosae, Rutaceae, Cucurbitaceae, Solanaceae, Piperaceae, Zingiberaceae, Lauraceae, Malvaceae, and Theaceae.

3. A particulate water-absorbing composition according to claim 1, wherein the plant powder comprises a spice.

4. A particulate water-absorbing composition according to claim 3, wherein the spice has a volume-average particle diameter of not larger than 850 μm.

5. A particulate water-absorbing composition according to claim 1, wherein the plant powder comprises a tea leaf and/or a residue of extraction therefrom.

6. A particulate water-absorbing composition according to claim 5, wherein the tea leaf and/or residue of extraction therefrom has a volume-average particle diameter of not larger than 500 μm.

7. A particulate water-absorbing composition according to claim 1, which exhibits an absorption capacity of 25 to 60 g/g for 0.9 weight % aqueous sodium chloride solution in 60 minutes, a suction index of not less than 14 g/g for 25 g of artificial urine (25° C.) under a load of 1.96 kPa, and an absorption rate of not more than 60 seconds for physiological salt solution of 30° C., wherein suction index (g/g) under load=initial suction power (g/g) under load in 3 minutes+suction power (g/g) under load in 60 minutes, and wherein said artificial urine has the following composition: 97.1 g of deionized water, 1.9 g of urea, 0.8 g of sodium chloride, 0.1 g of magnesium chloride hexahydrate, and 0.1 g of calcium chloride.

8. A particulate water-absorbing composition, which comprises a Tracheophyta plant powder and a water-absorbent resin, wherein the water-absorbent resin is a water-swellable and water-insoluble crosslinked poly(acrylic acid (salt)) polymer of 30 to 100 mol % in neutralization ratio and is contained in a proportion of not less than 70 weight % in the particulate water-absorbing composition, and wherein the particulate water-absorbing composition is in the range of 100 to 600 μm in weight-average particle diameter and not more than 10 weight % in proportion of particles having particle diameters of smaller than 106 μm and exhibits an absorption capacity of 25 to 60 g/g for 0.9 weight % aqueous sodium chloride solution in 60 minutes, a suction index of not less than 14 g/g for 25 g of artificial urine (25° C.) under a load of 1.96 kPa, and an absorption rate of not more than 60 seconds for physiological salt solution of 30° C., wherein suction index (g/g) under load=initial suction power (g/g) under load in 3 minutes+suction power (g/g) under load in 60 minutes, and wherein said artificial urine has the following composition: 97.1 g of deionized water, 1.9 g of urea, 0.8 g of sodium chloride, 0.1 g of magnesium chloride hexahydrate, and 0.1 g of calcium chloride, and wherein the Tracheophyta plant powder passes through a mesh having a mesh opening size of 850 μm; and wherein the content of the Tracheophyta plant powder is in the range of 0.001 to 20 weight parts per 100 weight parts of the solid content of the water-absorbent resin, and wherein said content of the Tracheophyta plant powder is an amount effective for the particulate water-absorbing composition to exhibit an offensive-odor removal index of not less than 180 wherein the offensive-odor removal index is represented by the following equation:

offensive-odor removal index=1.1×hydrogen sulfide removal ratio+2.0×methylmercaptan removal ratio+0.3×ammonia removal ratio.

9. A particulate water-absorbing composition according to claim 1, which is used for sanitary materials.

10. A process for producing a particulate water-absorbing composition, which comprises the step of adding a Tracheophyta plant powder to a water-absorbent resin in an amount of 0.001 to 20 weight parts per 100 weight parts of the solid content of the water-absorbent resin, wherein said amount of the Tracheophyta plant powder being added is an amount effective to provide the particulate water-absorbing composition with offensive-odor removal properties, wherein the Tracheophyta plant powder passes through a mesh having a mesh opening size of 850 μm, and wherein the water-absorbent resin is a water-swellable and water-insoluble crosslinked poly(acrylic acid (salt)) polymer of 30 to 100 mol % in neutralization ratio and is used in an amount so as to be contained in a proportion of not less than 70 weight % in the particulate water-absorbing composition and is in the range of 100 to 600 μm in weight-average particle diameter and not more than 10 weight % in proportion of particles having particle diameters of smaller than 106 μm and exhibits an absorption capacity of 25 to 60 g/g for 0.9 weight % aqueous sodium chloride solution in 60 minutes, a suction power of not less than 9 g/g for 25 g of artificial urine (25° C.) under a load of 1.96 kPa in 60 minutes, and an absorption rate of not more than 60 seconds for physiological salt solution of 30° C., wherein said artificial urine has the following composition: 97.1 g of deionized water, 1.9 g of urea, 0.8 g of sodium chloride, 0.1 g of magnesium chloride hexahydrate, and 0.1 g of calcium chloride.

11. An absorbent article, which comprises an absorbent layer, a liquid-permeable surface sheet, and a liquid-impermeable back sheet, wherein the absorbent layer includes the particulate water-absorbing composition as recited in claim 1.

12. An absorbent structure, which comprises a hydrophilic fiber, a Tracheophyta plant powder, and a water-absorbent resin, wherein the water-absorbent resin is a water-swellable and water-insoluble crosslinked poly(acrylic acid (salt)) polymer of 30 to 100 mol % in neutralization ratio and is in the range of 100 to 600 μm in weight-average particle diameter and not more than 10 weight % in proportion of particles having particle diameters of smaller than 106 μm and exhibits an absorption capacity of 25 to 60 g/g for 0.9 weight % aqueous sodium chloride solution in 60 minutes, a suction power of not less than 9 g/g for 25 g of artificial urine (25° C.) under a load of 1.96 kPa in 60 minutes, and an absorption rate of not more than 60 seconds for physiological salt solution of 30° C., wherein said artificial urine has the following composition: 97.1 g of deionized water, 1.9 g of urea, 0.8 g of sodium chloride, 0.1 g of magnesium chloride hexahydrate, and 0.1 g of calcium chloride, and wherein the Tracheophyta plant powder passes through a mesh having a mesh opening size of 850 μm, and wherein the content of the Tracheophyta plant powder is in the range of 0.001 to 20 weight parts per 100 weight parts of the solid content of the water-absorbent resin, and wherein said content of the Tracheophyta plant powder is an amount effective for a particulate water-absorbing composition to exhibit an offensive-odor removal index of not less than 180 as the particulate water-absorbing composition including a mixture of the Tracheophyta plant powder and the water-absorbent resin, wherein the offensive-odor removal index is represented by the following equation:

offensive-odor removal index=1.1×hydrogen sulfide removal ratio+2.0×methylmercaptan removal ratio+0.3×ammonia removal ratio.

13. An absorbent structure according to claim 12, which comprises the particulate water-absorbing composition in which the Tracheophyta plant powder is held by the water-absorbent resin, wherein the weight ratio of the particulate water-absorbing composition to the total of the hydrophilic fiber and the particulate water-absorbing composition is not less than 0.3.

14. A particulate water-absorbing composition according to claim 1, wherein the water-extractable content in the water-absorbent resin is not more than 50 weight %.

15. A particulate water-absorbing composition according to claim 1, wherein the Tracheophyta plant powder is in the range of 1 to 50 (but not including 50) in aspect ratio where the aspect ratio is calculated by length/breadth where the length and breadth are the dimensions of the Tracheophyta plant powder, and wherein the water content of the Tracheophyta plant powder is not more than 40%.

16. A particulate water-absorbing composition according to claim 8, which is used for sanitary materials.

17. An absorbent article, which comprises an absorbent layer, a liquid-permeable surface sheet, and a liquid-impermeable back sheet, wherein the absorbent layer includes the particulate water-absorbing composition as recited in claim 8.

18. A particulate water-absorbing composition according to claim 8, wherein the water-extractable content in the water-absorbent resin is not more than 50 weight %.

19. A particulate water-absorbing composition according to claim 8, wherein the Tracheophyta plant powder is in the range of 1 to 50 (but not including 50) in aspect ratio where the aspect ratio is calculated by length/breadth where the length and breadth are the dimensions of the Tracheophyta plant powder, and wherein the water content of the Tracheophyta plant powder is not more than 40%.

20. A particulate water-absorbing composition according to claim 1, wherein said Tracheophyta plant powder is a particulate and where said water-absorbent resin is a particulate, said composition comprising a dry blend of said Tracheophyta plant powder and said water-absorbent resin.

21. A particulate water-absorbing composition according to claim 8, wherein said composition is a dry blend of said Tracheophyta plant powder and said water-absorbent resin.

22. A particulate water-absorbing composition according to claim 21, wherein said Tracheophyta plant powder is a particulate and said water-absorbent resin is a particulate.

23. A process for producing a particulate water-absorbing composition according to claim 10, wherein said process comprises dry blending said Tracheophyta plant powder with said water-absorbent resin, wherein said Tracheophyta plant powder is a particulate and said water-absorbent resin is a particulate.

24. A particulate water-absorbing composition according to claim 1, further comprising an inorganic powder in an amount of 0.001 to 10 weight parts per 100 weight parts of the water-absorbent resin.

25. A particulate water-absorbing composition according to claim 8, further comprising an inorganic powder in an amount of 0.001 to 10 weight parts per 100 weight parts of the water-absorbent resin.

26. A particulate water-absorbing composition according to claim 1, which exhibits a color-difference (L, a, b) in which: L is not less than 40; the absolute value of a is not more than 4; and b is in the range of 0 to 15.

27. A particulate water-absorbing composition according to claim 8, which exhibits a color-difference (L, a, b) in which: L is not less than 40; the absolute value of a is not more than 4; and b is in the range of 0 to 15.

28. A particulate water-absorbing composition according to claim 8, wherein the Tracheophyta plant is at least one kind of Tracheophyta plant selected from the group consisting of Gramineae, maple family, Ebenaceae, Betulaceae, Compositae, Lamiaceae, cryptomeria family, Umbelliferae, Rosaceae, Vitaceae, Japanese cypress family, pine family, Fagaceae, Brassicaceae, Leguminosae, Rutaceae, Cucurbitaceae, Solanaceae, Piperaceae, Zingiberaceae, Lauraceae, Malvaceae, and Theaceae.

29. A particulate water-absorbing composition according to claim 8, wherein the Tracheophyta plant powder comprises a spice wherein the spice has a volume-average particle diameter of not larger than 850 μm.

30. A particulate water-absorbing composition according to claim 8, wherein the Tracheophyta plant powder comprises a tea leaf and/or a residue of extraction therefrom wherein the tea leaf and/or residue of extraction therefrom has a volume-average particle diameter of not larger than 500 μm.

31. A particulate water-absorbing composition according to claim 3, wherein the spice is at least one member selected from the group consisting of peppers, Japanese peppers, ginger, capsicums, parsley, and Japanese horseradishes.

32. A particulate water-absorbing composition according to claim 29, wherein the spice is at least one member selected from the group consisting of peppers, Japanese peppers, ginger, capsicums, parsley, and Japanese horseradishes.

33. A particulate water-absorbing composition according to claim 1, which has a powder odor strength of not more than 2.

34. A particulate water-absorbing composition according to claim 8, which has a powder odor strength of not more than 2.

35. A particulate water-absorbing composition according to claim 1, wherein the Tracheophyta plant powder is at least one member selected from the group consisting of pepper, Japanese pepper, ginger, parsley, green tea, milled green tea, oolong tea, pu-erh tea, a residue of extraction from green tea, a residue of extraction from black tea, a residue of extraction from oolong tea, citron, lime peel, mandarin orange peel, sea tangle, bamboo cuticle, a residue of extraction from coffee, strained grape lees, persimmon, mugwort, and bamboo.

36. A particulate water-absorbing composition according to claim 8, wherein the Tracheophyta plant powder is at least one member selected from the group consisting of pepper, Japanese pepper, ginger, parsley, green tea, milled green tea, oolong tea, pu-erh tea, a residue of extraction from green tea, a residue of extraction from black tea, a residue of extraction from oolong tea, citron, lime peel, mandarin orange peel, sea tangle, bamboo cuticle, a residue of extraction from coffee, strained grape lees, persimmon, mugwort, and bamboo.

37. A particulate water-absorbing composition according to claim 1, wherein the Tracheophyta plant powder is a bamboo powder.

38. A particulate water-absorbing composition according to claim 8, wherein the Tracheophyta plant powder is a bamboo powder.

39. A process for producing a particulate water-absorbing composition according to claim 10, wherein the Tracheophyta plant is at least one kind of Tracheophyta plant selected from the group consisting of Gramineae, maple family, Ebenaceae, Betulaceae, Compositae, Lamiaceae, cryptomeria family, Umbelliferae, Rosaceae, Vitaceae, Japanese cypress family, pine family, Fagaceae, Brassicaceae, Leguminosae, Rutaceae, Cucurbitaceae, Solanaceae, Piperaceae, Zingiberaceae, Lauraceae, Malvaceae, and Theaceae.

40. A process for producing a particulate water-absorbing composition according to claim 10, wherein the Tracheophyta plant powder comprises a spice wherein the spice has a volume-average particle diameter of not larger than 850 μm.

41. A process for producing a particulate water-absorbing composition according to claim 10, wherein the Tracheophyta plant powder comprises a tea leaf and/or a residue of extraction therefrom wherein the tea leaf and/or residue of extraction therefrom has a volume-average particle diameter of not larger than 500 μm.

42. A process for producing a particulate water-absorbing composition according to claim 10, wherein the Tracheophyta plant powder is at least one member selected from the group consisting of pepper, Japanese pepper, ginger, parsley, green tea, milled green tea, oolong tea, pu-erh tea, a residue of extraction from green tea, a residue of extraction from black tea, a residue of extraction from oolong tea, citron, lime peel, mandarin orange peel, sea tangle, bamboo cuticle, a residue of extraction from coffee, strained grape lees, persimmon, mugwort, and bamboo.

43. A particulate water-absorbing composition according to claim 1, wherein said content of the Tracheophyta plant powder is an amount effective for the particulate water-absorbing composition to remove hydrogen sulfide, methylmercaptan and ammonia from a liquid.

44. A particulate water-absorbing composition according to claim 8, wherein said content of the Tracheophyta plant powder is an amount effective for the particulate water-absorbing composition to remove hydrogen sulfide, methylmercaptan and ammonia from a liquid.

45. A process for producing a particulate water-absorbing composition according to claim 10, wherein said amount of the Tracheophyta plant powder being added is an amount effective for the particulate water-absorbing composition to remove hydrogen sulfide, methylmercaptan and ammonia from a liquid.

46. An absorbent structure according to claim 12, wherein said content of the Tracheophyta plant powder is an amount effective for the particulate water-absorbing composition to remove hydrogen sulfide, methylmercaptan and ammonia from a liquid.

* * * * *